(12) United States Patent
McCaffrey et al.

(10) Patent No.: US 11,266,425 B2
(45) Date of Patent: Mar. 8, 2022

(54) CAVITATION CATHETER

(71) Applicant: Medtronic Vascular, Inc., Santa Rosa, CA (US)

(72) Inventors: Gerry Oliver McCaffrey, Tuam (IE); Grainne Teresa Carroll, Galway (IE); Risa Tom Egerter, Galway (IE); Aran Murray, Galway (IE); Jonathan Ashley Cope, Santa Rosa, CA (US); Peter Glynn, Galway (IE); Christopher W. Storment, Sonoma, CA (US); Jack Wallis, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 217 days.

(21) Appl. No.: 16/661,561

(22) Filed: Oct. 23, 2019

(65) Prior Publication Data
US 2020/0129196 A1 Apr. 30, 2020

Related U.S. Application Data

(60) Provisional application No. 62/750,484, filed on Oct. 25, 2018.

(51) Int. Cl.
*A61B 17/22* (2006.01)
*A61B 17/00* (2006.01)
*A61M 25/00* (2006.01)

(52) U.S. Cl.
CPC ............... *A61B 17/22022* (2013.01); *A61B 2017/0019* (2013.01); *A61B 2017/00411* (2013.01);
(Continued)

(58) Field of Classification Search
CPC ........ A61B 17/22022; A61B 17/22012; A61B 2017/0019; A61B 2017/00411;
(Continued)

(56) References Cited

U.S. PATENT DOCUMENTS 5,016,808 A 5/1991 Heil, Jr. et al.
6,088,610 A 7/2000 Littmann
(Continued)

FOREIGN PATENT DOCUMENTS

WO 2018/075924 A1 4/2018

OTHER PUBLICATIONS

Extended European Search Report from counterpart European Application No. 19205267.8, dated Mar. 19, 2020, 5 pp.
(Continued)

*Primary Examiner* — Tan-Uyen T Ho
*Assistant Examiner* — Bridget E. Rabaglia
(74) *Attorney, Agent, or Firm* — Shumaker & Sieffert, P.A.

(57) ABSTRACT

A catheter assembly includes a catheter comprising a flexible elongated member including a distal portion that includes a tubular body defining an inner lumen and a plurality of body apertures that extend through a sidewall of the tubular body into the inner lumen, and a plurality of primary electrodes positioned along the tubular body. The catheter assembly includes a wire defining at least one secondary electrode, the wire being configured to be slidably moved through the inner lumen of the tubular body, where the wire and the plurality of primary electrodes are configured to electrically couple to an energy source that delivers an electrical pulse to a fluid in contact with the plurality of primary electrodes and the at least one secondary electrode to cause the fluid to undergo cavitation to generate a pressure pulse wave within the fluid.

27 Claims, 14 Drawing Sheets

(52) U.S. Cl.
CPC ........... *A61B 2017/22008* (2013.01); *A61B 2017/22038* (2013.01); *A61B 2017/22074* (2013.01); *A61M 25/007* (2013.01); *A61M 25/0074* (2013.01)

(58) Field of Classification Search
CPC ........... A61B 2017/22008; A61B 2017/22038; A61B 2017/22074; A61B 2017/2201; A61B 2017/22025; A61B 2017/22007; A61M 25/007; A61M 25/0074
USPC ............................................ 606/128
See application file for complete search history.

(56) References Cited

U.S. PATENT DOCUMENTS

| | | | |
|---|---|---|---|
| 8,197,463 B2 | 6/2012 | Intoccia | |
| 8,244,378 B2 | 8/2012 | Bly et al. | |
| 8,540,729 B2 | 9/2013 | Teague et al. | |
| 8,600,472 B2 | 12/2013 | Govari et al. | |
| 9,192,435 B2 | 11/2015 | Jenson | |
| 9,351,790 B2 | 5/2016 | Zemel et al. | |
| 9,452,017 B2 | 9/2016 | Chang et al. | |
| 9,642,673 B2 | 5/2017 | Adams et al. | |
| 9,717,513 B2 | 9/2017 | Golan | |
| 9,814,476 B2 | 11/2017 | Adams et al. | |
| 2007/0250143 A1 | 10/2007 | Sommer | |
| 2010/0023088 A1 | 1/2010 | Stack et al. | |
| 2014/0005576 A1 | 1/2014 | Adams et al. | |
| 2014/0031661 A1 | 1/2014 | Clark et al. | |
| 2014/0046229 A1 | 2/2014 | Hawkins et al. | |
| 2014/0066915 A1* | 3/2014 | Zhou | A61B 18/18 606/33 |
| 2014/0243809 A1* | 8/2014 | Gelfand | A61B 18/16 606/28 |
| 2015/0039002 A1 | 2/2015 | Hawkins | |
| 2015/0320432 A1 | 11/2015 | Adams | |
| 2016/0135828 A1 | 5/2016 | Hawkins et al. | |
| 2017/0135709 A1 | 5/2017 | Nguyen et al. | |
| 2017/0258523 A1 | 9/2017 | Adams et al. | |
| 2017/0303946 A1 | 10/2017 | Ku et al. | |
| 2018/0153568 A1 | 6/2018 | Kat Kuoy | |

OTHER PUBLICATIONS

U.S. Appl. No. 16/661,736, filed Oct. 23, 2019, naming inventors McCaffrey et al.

* cited by examiner

CAVITATION CATHETER

This application claims the benefit of U.S. Provisional Application No. 62/750,484, which was filed on Oct. 25, 2018, and is entitled, "CAVITATION CATHETER." The entire content of U.S. Provisional Application No. 62/750, 484 is incorporated herein by reference.

TECHNICAL FIELD

This disclosure relates to medical catheters.

BACKGROUND

Medical catheters have been proposed for use with various medical procedures. For example, medical catheters may be used to access and treat defects in blood vessels, such as, but not limited to, treatment of calcific atherosclerotic plaque buildup within the vasculature wall of vasculature associated with cardiovascular disease. Some techniques for treating such diseases may include balloon angioplasty alone or balloon angioplasty followed by stenting of the vasculature. However, such techniques may fail to address certain types of plaque buildup and/or result in re-stenotic events.

SUMMARY

In some aspects, the disclosure describes catheters and catheter assemblies, such as intravascular catheters, that include a plurality of electrodes mounted to and forming part of the exterior of an elongated tubular body. An energy source may be configured to deliver energy intravascularly to a fluid in contact with the electrodes to induce cavitation within the fluid in the vasculature of a patient. The cavitation may be used to treat a defect in the vasculature of the patient. For example, the cavitation may produce a high-energy pressure pulse wave that, when directed at a vasculature wall, may be used to disrupt and fracture calcific atherosclerotic plaque buildup within the vasculature wall. The disruption and fracture of the plaque may allow the vasculature to be more easily expanded to achieve better blood flow through the vessel. In some examples, the use of such devices may reduce or eliminate the need for subsequent stenting of the vasculature and reduce the chance of restenosis. In some other aspects, the disclosure describes methods of using the catheters described herein.

Clause 1: In one example, a catheter assembly includes a catheter including a flexible elongated member including a distal portion, the distal portion including a tubular body defining an inner lumen, the tubular body defining a plurality of body apertures that extend through a sidewall of the tubular body into the inner lumen and a plurality of primary electrodes positioned along the tubular body. The catheter assembly includes a wire defining at least one secondary electrode, the wire being configured to be slidably moved through the inner lumen of the tubular body, where the wire and the plurality of primary electrodes are configured to electrically couple to an energy source that delivers an electrical pulse to a fluid in contact with the plurality of primary electrodes and the at least one secondary electrode to cause the fluid to undergo cavitation to generate a pressure pulse wave within the fluid.

Clause 2: In some of the examples of the catheter assembly of clause 1, the catheter assembly further includes an energy source electrically coupled to the plurality of primary electrodes and the wire, where the catheter assembly and the energy source are configured such that, when the at least one secondary electrode is aligned with a respective body aperture of the plurality of body apertures while in the inner lumen of the tubular body, the energy source delivers an electrical pulse between a respective primary electrode of the plurality of primary electrodes adjacent to the respective body aperture and the at least one secondary electrode to cause the fluid in direct contact with the respective primary electrode and the at least one secondary electrode to undergo cavitation to generate the pressure pulse wave within the fluid.

Clause 3: In some of the examples of the catheter assembly of clause 1 or 2, a surface of each primary electrode of the plurality of primary electrodes is exposed to an external environment of the catheter.

Clause 4: In some of the examples of the catheter assembly of clause 3, the surface of each primary electrode of the plurality of primary electrodes forms an exterior surface of the catheter that defines a surface area of less than 0.1 mm$^2$.

Clause 5: In some of the examples of the catheter assembly of any one of clauses 1 to 4, the tubular body is configured to change from a collapsed configuration to a curvilinear configuration.

Clause 6: In some of the examples of the catheter assembly of clause 5, where, when the tubular body is in the curvilinear configuration, at least a portion of the tubular body forms a helical-shape.

Clause 7: In some of the examples of the catheter assembly of any one of clauses 1 to 6, further including an electrically insulating sheath over the wire, a portion of the wire being exposed to form the at least one secondary electrode.

Clause 8: In some of the examples of the catheter assembly of any one of clauses 1 to 7, further including at least one electrical conductor within the tubular body, the at least one electrical conductor being configured to electrically connect the energy source to at least one electrode of the plurality of primary electrodes.

Clause 9: In some of the examples of the catheter assembly of clause 8, each primary electrode of the plurality of primary electrodes is electrically coupled to the at least one electrical conductor.

Clause 10: In some of the examples of the catheter assembly of any one of clauses 1 to 9, each primary electrode of the plurality of primary electrodes includes an electrically conducive band coupled to the tubular body.

Clause 11: In some of the examples of the catheter assembly of any one of clauses 1 to 10, each primary electrode of the plurality of primary electrodes defines an electrode aperture that extends through the primary electrode and aligns with a corresponding body aperture of the plurality of body apertures.

Clause 12: In some of the examples of the catheter assembly of clause 11, for each primary electrode of the plurality of primary electrodes, the electrode aperture and the corresponding body aperture provide fluid communication between a surface of the primary electrode and the inner lumen.

Clause 13: In some of the examples of the catheter assembly of any one of clauses 1 to 8, the tubular body further includes an electrically conductive support structure or shape member configured to electrically connect to the energy source, where the plurality of body apertures extend through the sidewall of the tubular body and the electrically conductive support structure or shape member, where, for each respective body aperture of the plurality of body apertures, a surface of the electrically conductive support structure or shape member is exposed by the respective body aperture and forms a respective primary electrode of the plurality of primary electrodes.

Clause 14: In some of the examples of the catheter assembly of any one of clauses 1 to 13, the elongated member is configured to position the plurality of primary electrodes in direct contact with a bodily fluid of a patient when deployed in vasculature of the patient.

Clause 15: In some of the examples of the catheter assembly of any one of clauses 1 to 14, the wire includes a guidewire.

Clause 16: In some of the examples of the catheter assembly of any one of clauses 1 to 15, where, to deliver the energy signal, the energy source is configured to deliver a plurality of electrical pulses each having a pulse width between about 1 microsecond (µs) and about 200 µs.

Clause 17: In one example, a catheter assembly includes a catheter including a flexible elongated member including a distal portion, the distal portion including a tubular body including an inner liner, an electrically conductive support structure or shape member, and an outer jacket, where the tubular body defines an inner lumen, where the tubular body defines a plurality of body apertures that extend through a sidewall of the tubular body including the electrically conductive support structure or shape member into the inner lumen, and a plurality of primary electrodes, where, within each respective body aperture of the plurality of body apertures, the electrically conductive support structure or shape member defines an exposed surface that forms a respective primary electrode of the plurality of primary electrodes. The catheter assembly includes a wire including at least one secondary electrode, the wire being configured to be slidably moved through the inner lumen of the tubular body, where the wire and the electrically conductive support structure or shape member are configured to electrically couple to an energy source that delivers an electrical pulse to a fluid in contact with the plurality of primary electrodes and the at least one secondary electrode to cause the fluid to undergo cavitation to generate a pressure pulse wave within the fluid.

Clause 18: In some of the examples of the catheter assembly of clause 17, further including an energy source electrically coupled to the electrically conductive support structure or shape member and the wire, where the catheter assembly and the energy source are configured such that, when the at least one secondary electrode is aligned with a respective body aperture of the plurality of body apertures while in the inner lumen of the tubular body, the energy source delivers an electrical pulse between a respective primary electrode of the plurality of primary electrodes and the at least one secondary electrode to cause the fluid in direct contact with the respective primary electrode and the at least one secondary electrode to undergo cavitation to generate the pressure pulse wave within the fluid.

Clause 19: In some of the examples of the catheter assembly of clause 17 or 18, a surface of each primary electrode of the plurality of primary electrodes is exposed to an external environment of the catheter.

Clause 20: In some of the examples of the catheter assembly of any one of clauses 17 to 19, the tubular body is configured to change from a collapsed configuration to a curvilinear configuration.

Clause 21: In some of the examples of the catheter assembly of clause 20, where, when the tubular body is in the curvilinear configuration, at least a portion of the tubular body forms a helical-shape.

Clause 22: In some of the examples of the catheter assembly of any one of clauses 17 to 21, further including an electrically insulating sheath over the wire, a portion of the wire being exposed to form the at least one secondary electrode.

Clause 23: In one example, a method includes introducing a catheter through vasculature of a patient to a target treatment site, the catheter including a flexible elongated member including a distal portion, the distal portion including a tubular body defining an inner lumen, the tubular body defining a plurality of body apertures that extend through a sidewall of the tubular body into the inner lumen; and a plurality of primary electrodes positioned along the tubular body. The method includes positioning the distal portion of the elongated member adjacent to the target treatment site; slidably maneuvering a wire including at least one secondary electrode within the inner lumen of the elongated member to align the at least one secondary electrode of the wire with a respective body aperture of the plurality of body apertures, the respective body aperture being adjacent to a respective primary electrode of the plurality of primary electrodes; and delivering, using an energy source, an electrical pulse between the respective primary electrode and the at least one secondary electrode, where delivery of the electrical pulse causes a fluid in direct contact with the respective primary electrode and the at least one secondary electrode to undergo cavitation that results in the generation of a pressure pulse wave within the fluid.

Clause 24: In some of the examples of the method of clause 23, further including after delivering the electrical pulse, slidably maneuvering the wire within the inner lumen of the elongated member to align the at least one secondary electrode of the wire with a second respective body aperture of the plurality of body apertures, the second respective body aperture being adjacent to a second respective primary electrode of the plurality of primary electrodes; and delivering a second electrical pulse using the energy source, where the electrical pulse is transmitted between the second respective primary electrode and the at least one secondary electrode through a fluid in direct contact with the second respective primary electrode and the at least one secondary electrode, the electrical pulse configured to cause the fluid to undergo cavitation to generate a pressure pulse wave within the fluid.

Clause 25: In some of the examples of the method of clause 23, where delivering, using an energy source, an electrical pulse between the respective primary electrode and the at least one secondary electrode includes delivering, using the energy source, an electrical pulse between each of the primary electrodes and the at least one secondary electrode at the same time to cause the fluid to undergo cavitation to generate a pressure pulse wave within the fluid.

Clause 26: In some of the examples of the method of any one of clauses 23 to 25, where delivering, using the energy source, the electrical pulse includes delivering a plurality of electrical pulses having a pulse width between about 1 microsecond (µs) and about 200 µs.

Clause 27: In some of the examples of the method of any one of clauses 23 to 26, where delivering, using the energy source, the electrical pulse between the respective primary electrode and the at least one secondary electrode includes delivering the electrical pulse through a fluid in direct contact with the vasculature of the patient.

Clause 28: In some of the examples of the method of any one of clauses 23 to 27, a surface of each primary electrode of the plurality of primary electrodes is exposed to an external environment of the catheter.

Clause 29: In some of the examples of the method of any one of clauses 23 to 28, the tubular body is configured to change from a collapsed configuration to a curvilinear configuration.

Clause 30: In some of the examples of the method of any one of clauses 23 to 29, the wire includes an electrically insulating sheath over the wire, a portion of the wire being exposed to form the at least one secondary electrode.

Clause 31: In some of the examples of the method of any one of clauses 23 to 30, where delivering, using the energy source, the electrical pulse between the respective primary electrode and the at least one secondary electrode includes delivering the electrical pulse through the fluid contained within the respective body aperture.

Clause 32: In some of the examples of the method of any one of clauses 23 to 31, each primary electrode of the plurality of primary electrodes defines an electrode aperture that extends through the primary electrode and aligns with a corresponding body aperture of the plurality of body apertures.

Clause 33: In some of the examples of the method of any one of clauses 23 to 31, the tubular body further includes an electrically conductive support structure or shape member configured to electrically connect to the energy source, where the plurality of body apertures extend through the sidewall of the tubular body and the electrically conductive support structure or shape member, where, for each respective body aperture of the plurality of body apertures, a surface of the electrically conductive support structure or shape member is exposed by the respective body aperture and forms a respective primary electrode of the plurality of primary electrodes.

Clause 34: In some of the examples of the method of any one of clauses 23 to 31, each primary electrode of the plurality of primary defines an exposed surface area of less than about 0.1 mm$^2$.

Clause 35: In one example, a catheter assembly includes a flexible elongated member including a distal portion, the distal portion including a tubular body defining an inner lumen, the tubular body being configured to change from a collapsed configuration to a curvilinear configuration, the tubular body defining a plurality of body apertures that extend through a sidewall of the tubular body into the inner lumen; and a plurality of primary electrodes on the tubular body. The catheter assembly includes a wire including a secondary electrode, the wire being configured to be slidably moved through the inner lumen of the tubular body and an energy source electrically coupled to the plurality of primary electrodes of the elongated member and electrically coupled to the secondary electrode of the wire, where the catheter assembly and the energy source are configured such that, when the secondary electrode is aligned with a respective body aperture of the plurality of body apertures while in the inner lumen of the tubular body, the energy source delivers an electrical pulse between a respective primary electrode of the plurality of primary electrodes adjacent to the respective body aperture and the secondary electrode to cause a fluid in direct contact with the respective primary electrode and the secondary electrode to undergo cavitation to generate a pressure pulse wave within the fluid.

Clause 36: In some of the examples of the catheter assembly of clause 35, each electrode of the plurality of primary electrodes defines an electrode aperture that extends through the electrode and aligns with a corresponding body aperture of the plurality of body apertures.

Clause 37: In some of the examples of the catheter assembly of clause 35 or 36, where, when the tubular body is in the curvilinear configuration, at least a portion of the tubular body forms a helical-shape.

Clause 38: In some of the examples of the catheter assembly of clause 37, where, when the distal portion of the elongated member is in the curvilinear configuration, each electrode aperture of the plurality of primary electrodes faces toward a central longitudinal axis of the helical-shape.

Clause 39: In some of the examples of the catheter assembly of clause 37 or 38, where, when the distal portion of the elongated member is in the curvilinear configuration, adjacent primary electrodes of the plurality of primary electrodes are spaced along the helical-shape at between about 90° to about 120° intervals relative to a rotation of the helical-shape.

Clause 40: In some of the examples of the catheter assembly of any one of clauses 36 to 39, each primary electrode of the plurality of primary electrodes includes a cylindrical body, the cylindrical body including at least one surface protrusion extending radially outward from the cylindrical body of the electrodes and positioned on a radially opposite side of the cylindrical body to the electrode aperture.

Clause 41: In some of the examples of the catheter assembly of any one of clauses 36 to 40, where for each primary electrode of the plurality of primary electrodes, the electrode aperture and the corresponding body aperture facilitate fluid communication between a surface of each primary electrode and the wire.

Clause 42: In some of the examples of the catheter assembly of clause 41, the surface of each primary electrode forms a portion of an exterior of the flexible elongated member.

Clause 43: In some of the examples of the catheter assembly of any one of clauses 35 to 42, further including an electrically insulating sheath over the wire, a portion of the wire being exposed to form the secondary electrode.

Clause 44: In some of the examples of the catheter assembly of any one of clauses 35 to 43, further including at least one electrical conductor within the tubular body, the at least one electrical conductor being configured to electrically connect the energy source to the plurality of primary electrodes.

Clause 45: In some of the examples of the catheter assembly of clause 44, the electrodes of the plurality of primary electrodes are electrically coupled in series via the at least one conductor.

Clause 46: In some of the examples of the catheter assembly of any one of clauses 35 to 45, the tubular body includes a shape memory material configured to change the tubular body from the collapsed configuration to the curvilinear configuration.

Clause 47: In some of the examples of the catheter assembly of any one of clauses 35 to 45, further including a sheath disposed over the distal portion of the elongated member, the sheath being configured to maintain the distal portion of the elongated member in the collapsed configuration while disposed over the distal portion, the sheath is configured to be proximally retracted relative to the distal portion of the elongated member.

Clause 48: In some of the examples of the catheter assembly of clause 47, the elongated member is configured to transition to the curvilinear configuration in response to retraction of the sheath proximally past the distal portion of the elongated member.

Clause 49: In some of the examples of the catheter assembly of any one of clauses 35 to 48, the wire includes a proximal portion and a distal portion, and wherein the tubular body includes a shape-recovery force sufficient to overcome a straightening force provided by the distal portion of the wire to transform the distal portion of the elongated member to the curvilinear configuration when the distal end of the wire is aligned or proximal to a distal end of the elongated member.

Clause 50: In some of the examples of the catheter assembly of clause 49, the proximal portion of the wire is configured to maintain the distal portion of the elongated member in the collapsed configuration while the proximal portion of the wire is disposed within an inner lumen of the distal portion of the elongated member.

Clause 51: In some of the examples of the catheter assembly of any one of clauses 35 to 50, the elongated member is configured to position the plurality of primary electrodes in direct contact with a bodily fluid of a patient when deployed in vasculature of the patient.

Clause 52: In some of the examples of the catheter assembly of any one of clauses 35 to 51, at least a portion of each primary electrode of the plurality of primary electrodes forms an exterior surface of the elongated member.

Clause 53: In some of the examples of the catheter assembly of any one of clauses 35 to 52, where, to deliver the energy signal, the energy source is configured to deliver a plurality of electrical pulses having a pulse width of between about 1 microsecond (μs) and about 200 μs.

Clause 54: In one example, a method includes positioning a distal portion of a flexible elongated member of a catheter in a curvilinear configuration, the catheter includes the flexible elongated member including the distal portion, the distal portion including a tubular body defining an inner lumen, the tubular body being configured to change from a collapsed configuration to a curvilinear configuration, the tubular body defining a plurality of body apertures that extend through a sidewall of the tubular body into the inner lumen and a plurality of primary electrodes on the tubular body. The method includes slidably maneuvering a wire including a secondary electrode within the inner lumen of the elongated member to align the secondary electrode of the wire with a respective body aperture of the plurality of body apertures, the respective body aperture being adjacent to a respective primary electrode of the plurality of primary electrodes and delivering, using an energy source, an electrical pulse across the respective primary electrode and the secondary electrode, where delivery of the electrical pulse causes a fluid in direct contact with the respective primary electrode and the secondary electrode to undergo cavitation that results in the generation of a pressure pulse wave within the fluid.

Clause 55: In some of the examples of the method of clause 54, each electrode of the plurality of primary electrodes defines an electrode aperture that extends through the electrode and aligns with a corresponding body aperture of the plurality of body apertures.

Clause 56: In some of the examples of the method of clause 54 or 55, positioning the distal portion of the flexible elongated member of the catheter in the curvilinear configuration includes introducing the distal portion through a delivery sheath, the delivery sheath maintains the distal portion of the elongated member in the collapsed configuration until the distal portion moved past a distal end of the delivery sheath to allow the distal portion to transition to the curvilinear configuration.

Clause 57: In some of the examples of the method of clause 56, further including, after delivering the electrical pulse, moving the distal portion of the elongated member into a lumen of the delivery sheath and withdrawing the catheter from the vasculature of the patient.

Clause 58: In some of the examples of the method of any one of clauses 54 to 57, when the tubular body is in the curvilinear configuration, at least a portion of the tubular body forms a helical-shape.

Clause 59: In some of the examples of the method of clause 58, when the distal portion of the elongated member is in the curvilinear configuration, each electrode aperture of the plurality of primary electrodes face toward a central longitudinal axis of the helical-shape.

Clause 60: In some of the examples of the method of any one of clauses 55 to 59, each primary electrode of the plurality of primary electrodes includes a cylindrical body, the cylindrical body including at least one surface protrusion extending radially outward from the cylindrical body of the electrodes and positioned on a radially opposite side of the cylindrical body to the electrode aperture.

Clause 61: In some of the examples of the method of any one of clauses 54 to 60, the energy source is configured to deliver a plurality of electrical pulses having a pulse width of between about 1 microsecond (μs) and about 200 μs.

Clause 62: In some of the examples of the method of any one of clauses 54 to 61, further includes after delivering the electrical pulse, slidably maneuvering the wire within the inner lumen of the elongated member to align the secondary electrode of the wire with a second respective body aperture of the plurality of body apertures, the second respective body aperture being adjacent to a respective second primary electrode of the plurality of primary electrodes, and delivering a second electrical pulse using the energy source, where the electrical pulse is transmitted between the respective second primary electrode and the secondary electrode through a fluid in direct contact with the respective second primary electrode and the secondary electrode, the electrical pulse configured to cause the fluid to undergo cavitation to generate a pressure pulse wave within the fluid.

Clause 63: In some of the examples of the method of any one of clauses 54 to 62, further including introducing the elongated member through vasculature of a patient to a target treatment site and positioning the distal portion of the elongated member in the curvilinear configuration adjacent to the target treatment site.

Clause 64: In one example, a catheter assembly includes a catheter including a flexible elongated member including a distal portion, the distal portion winding around a central longitudinal axis to define a helical-shape, the distal portion including a tubular body defining an inner lumen, the tubular body defining a plurality of body apertures that extend through a sidewall of the tubular body into the inner lumen and a plurality of primary electrodes on the tubular body. The catheter assembly includes a wire including a secondary electrode, the wire being configured to be slidably moved through the inner lumen of the tubular body.

Clause 65: In some of the examples of the catheter assembly of clause 64, each electrode of the plurality of primary electrodes defines an electrode aperture that extends through the electrode and aligns with a corresponding body aperture of the plurality of body apertures.

Clause 66: In some of the examples of the catheter assembly of clause 64 or 65, the catheter assembly includes an energy source electrically coupled to the plurality of primary electrodes of the elongated member and electrically coupled to the secondary electrode of the wire, where the catheter assembly is configured such that when the secondary electrode is aligned with a respective body aperture of the plurality of body apertures while in the inner lumen of the tubular body, the energy source can deliver an electrical pulse between a respective primary electrode of the plurality of primary electrodes and the secondary electrode through a fluid in direct contact with the respective primary electrode and the secondary electrode to cause the fluid to undergo cavitation to generate a pressure pulse wave within the fluid.

Clause 67: In some of the examples of the catheter assembly of any one of clauses 64 to 66, the helical-shape includes a helix diameter of about 1 mm to about 30 mm and a pitch of about 0.6 mm to about 5 mm.

Clause 68: In some of the examples of the catheter assembly of any one of clauses 64 to 67, a ratio of a diameter of helical-shape to a diameter of the tubular body is between about 2:1 to about 30:1.

Clause 69: In some of the examples of the catheter assembly of any one of clauses 64 to 68, each electrode aperture of the plurality of primary electrodes face toward the central longitudinal axis of the helical-shape.

Clause 70: In some of the examples of the catheter assembly of any one of clauses 64 to 69, adjacent primary electrodes of the plurality of primary electrodes are spaced along the helical-shape at between about 90° to about 120° intervals relative to a rotation of the helical-shape.

Clause 71: In some of the examples of the catheter assembly of any one of clauses 65 to 70, each primary electrode of the plurality of primary electrodes includes a cylindrical body, the cylindrical body including at least one surface protrusion extending radially outward from the cylindrical body of the electrodes and positioned on a radially opposite side of the cylindrical body to the electrode aperture.

Clause 72: In some of the examples of the catheter assembly of clause 71, each of the at least one surface protrusions of the plurality or primary electrodes faces radially outward relative to the helical-shape.

Clause 73: In some of the examples of the catheter assembly of any one of clauses 64 to 72, a surface of each primary electrode forms a portion of an exterior of the catheter.

Clause 74: In some of the examples of the catheter assembly of any one of clauses 64 to 73, the distal portion of the elongated member being configured to collapse to form a substantially linear profile.

Clause 75: In some of the examples of the catheter assembly of any one of clauses 64 to 74, the tubular body includes a shape memory material pre-set in the helical-shape.

The details of one or more examples are set forth in the accompanying drawings and the description below. Other features, objects, and advantages of examples according to this disclosure will be apparent from the description and drawings, and from the claims.

DETAILED DESCRIPTION

This disclosure describes medical device assemblies, such as intravascular catheters, that include a flexible elongated member configured to be navigated through vasculature of a patient with the assistance of a delivery sheath or guidewire, to a target treatment site within the vasculature. The elongated member includes a distal portion that includes a tubular body and one or more primary electrodes carried along the tubular body that are each connected to an external energy source. The primary electrodes are configured to intravascularly deliver energy (e.g., electrical energy) to a fluid within the vessel that may cause the fluid to rapidly heat and produce a short-lived gaseous steam/plasma bubble that quickly collapses (e.g., cavitates), releasing energy in the form of a pressure pulse wave into the vessel.

The pressure pulse wave may be used to treat a defect in the vasculature of the patient at the target treatment site. In some examples, the target treatment site may be a site within the vasculature that has a defect that may be affecting blood flow through the vasculature. For example, the target treatment site may be a portion of the vasculature wall that includes a calcified lesion, e.g., calcific atherosclerotic plaque buildup. A calcified lesion can cause partial or full blockages of blood bearing vasculatures, which can result in adverse physiological effects to the patient. Such lesions may be very hard and difficult to treat using traditional methods, such as balloon angioplasty, stenting, thrombectomy, atherectomy, or other interventional procedures. The pressure pulse wave resulting from the cavitation procedure using a catheter described herein may impact the calcified lesion (or other defect at the treatment site) to fracture or disrupt at least part of the lesion. This treatment of the calcified lesion may be used in conjunction with a treatment balloon to help open-up the blood vessel of the patient, improving blood flow in the blood vessel. For example, the treatment of the calcified lesion using the catheters described herein may help restore the vasculature to a normal or at least increased flow diameter.

Figure 1A:
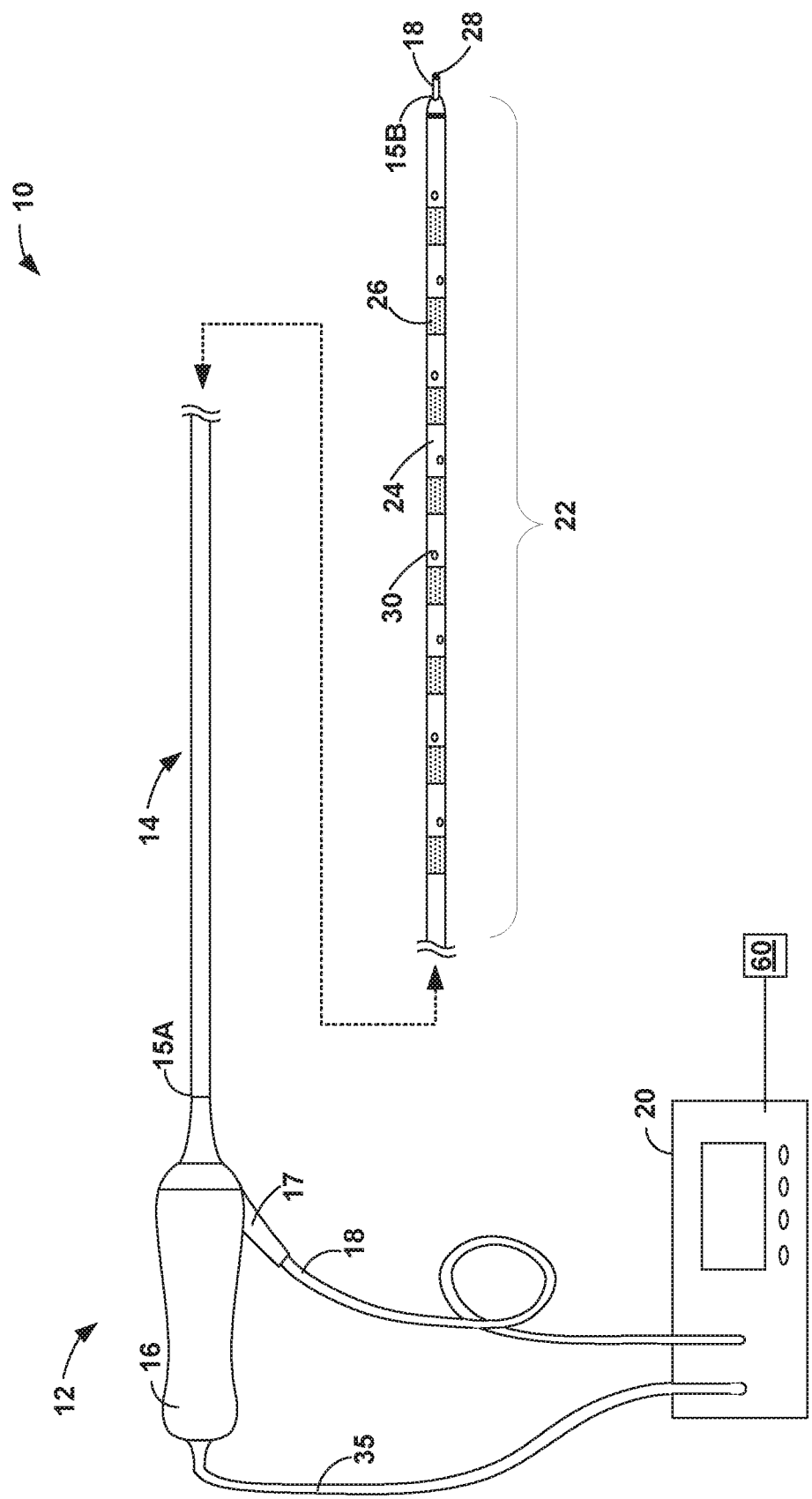
FIGS. 1A-1C are schematic views of an example catheter assembly that includes a catheter comprising an elongated member and a hub portion, and an energy source electrically coupled to the catheter.
Figure 1B:
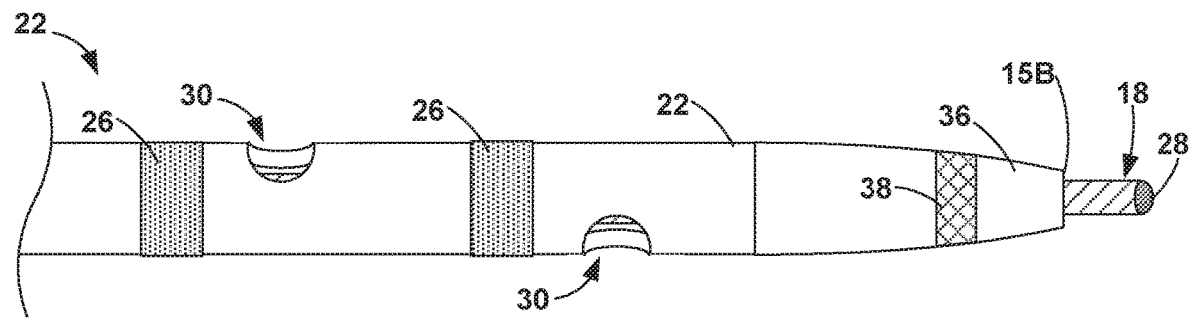
Figure 1C:
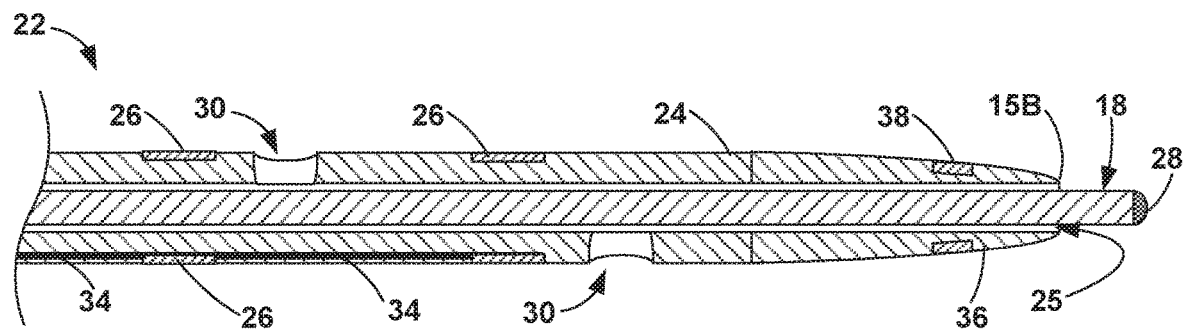

Various details of the catheter assemblies are discussed below with respect to reference to FIGS. 1A-11C. FIGS. 1A-1C are schematic views of an example catheter assembly 10, which includes a catheter 12 comprising an elongated member 14 and hub portion 16, a wire 18 (e.g., a guide wire), and an energy source 20 electrically coupled to catheter 12 and wire 18. Elongated member 14 of catheter 12 extends from a proximal end 15A to a distal end 15B with proximal end 15A connected to hub portion 16. Elongated member 14 includes a distal portion 22 comprising a tubular body 24 that defines an inner lumen 25 and includes one or more primary electrodes 26 positioned along tubular body 24. Wire 18 includes at least one secondary electrode 28 and may be slidably disposed within inner lumen 25. FIGS. 1B and 1C provide greater detail of distal portion 22 of catheter 12, illustrating both a side view (FIG. 1B) and a cross-sectional side view (FIG. 1C) of distal portion 22.

As described further below, energy source 20 is configured to deliver electrical energy between one or more of primary electrodes 26 and secondary electrode 28 located on wire 18. The electrical energy is passed between one or more of primary electrodes 26 and secondary electrode 32 using fluid contained within a vessel of the patient as the conductive medium to induce cavitation of the fluid and deliver therapy to a calcified lesion on or within the vessel wall using a pressure pulse wave created by the cavitation of the fluid. To facilitate the electrical connection between primary electrodes 26 and secondary electrode 28 portions of primary electrodes 26 and secondary electrode 28 may be in non-direct contact with each other (e.g., separated by an electrically insulative material) but may each be exposed to the fluid contained within the vessel of patient. For example, each of primary electrodes 26 may include at least one exposed surface that lies in direct contact with the fluid, such as a bodily fluid (e.g., blood) or introduced fluid (e.g., saline), contained within the vasculature of the patient. The designation of a "primary" or a "secondary" electrode is used to merely differentiate one set of electrodes from another and is not intended to indicate a preference among the electrodes, limit the direction in which an electrical signal (e.g., an electrical pulse) is transmitted from one electrode to another, or designate where the cavitation initiates unless described otherwise in the examples.

In some examples, catheter 12 may be used to access relatively distal vasculature locations in a patient or other relatively distal tissue sites (e.g., relative to the vasculature access point). Example vasculature locations may include, for example, locations in a coronary artery, peripheral vasculature (e.g., carotid, iliac, or femoral artery, or a vein), or cerebral vasculature, or a heart valve (e.g., aortic valve, mitral valve, pulmonic valve, tricuspid valve, or the like). In some examples, elongated member 14 is structurally configured to be relatively flexible, pushable, and relatively kink- and buckle-resistant, so that it may resist buckling when a pushing force is applied to a relatively proximal portion of catheter 12 to advance elongated member 14 distally through vasculature, and so that it may resist kinking when traversing around a tight turn in the vasculature. Unwanted kinking and/or buckling of elongated member 14 may hinder a clinician's efforts to push the catheter body distally, e.g., past a turn in the vasculature.

Elongated member 14 may have any suitable length for accessing a target tissue site within the patient from a vasculature access point. The length may be measured along the longitudinal axis of elongated member 14. The working length of elongated member 14 may depend on the location of the calcified lesion within vasculature. For example, if catheter 12 is a catheter used to access a coronary, carotid, or abdominal artery, elongated member 14 may have a working length of about 50 centimeters (cm) to about 200 cm, such as about 110 cm, although other lengths may be used. In other examples, or for other applications, the working length of elongated member 14 may have different lengths. In some examples, the length of distal portion 22 that includes primary electrodes 26 may have a total length of about 5 mm to about 50 mm in order to accommodate the length of calcified lesion 44.

The outer diameter of elongated member 14 (e.g., the cross-sectional diameter of tubular body 24) may be of any suitable size or dimension including, for example, between about 1 millimeter (mm) and about 12 mm. In some examples, catheter 12 may be characterized as a low-profile catheter having an outer diameter along distal portion 22 of about 0.3 mm to about 2 mm. The low-profile nature of catheter 12 may allow elongated member 14 to be navigated through particularly narrow or occlude vessels within the patient to treat calcified lesions with reduced openings.

In some examples, at least a portion of an outer surface of elongated member 14 may include one or more coatings, such as, but not limited to, an anti-thrombogenic coating, which may help reduce the formation of thrombi in vitro, an anti-microbial coating, and/or a lubricating coating. In some examples, the entire working length of elongated member 14 may be coated with the hydrophilic coating. In other examples, only a portion of the working length of elongated member 14 coated with the hydrophilic coating. This may provide a length of elongated member 14 distal to hub portion 16 with which the clinician may grip elongated member 14, e.g., to rotate elongated member 14 or push elongated member 14 through vasculature. In some examples, the entire working length of elongated member 14 or portions thereof may include a lubricious outer surface, e.g., a lubricious coating. The lubricating coating may be configured to reduce static friction and/or kinetic friction between elongated member 14 and the interior wall of delivery catheter or the tissue of the patient as elongated member 14 is advanced through the vasculature.

Elongated member 14 may also include one or more radiopaque markers 38 which may help a clinician determine the positioning of elongated member 14 relative to relative to a target treatment site using ultrasound or other suitable technique. For example, one or more radiopaque markers 38 may be positioned along distal portion 22 such as near distal end 15B, adjacent to one or more of primary electrodes 26 or body apertures 30, or the like. In some examples, one or more of primary electrodes 26 may act as radiopaque markers 38.

The proximal portion of elongated member 14 may be received within hub portion 16 and can be mechanically connected to hub portion 16 via an adhesive, welding, or another suitable technique or combination of techniques. Hub portion 16 may serve as a handle for catheter 12 allowing the clinician to grasp catheter 12 at hub portion 16 and advance distal portion 22 through vasculature of a patient. In some examples, catheter 12 can include another structure in addition or instead of hub portion 16. For example, catheter 12 or hub portion 16 may include one or more luers or other mechanisms (e.g., access ports 17) for establishing connections between catheter 12 and other devices. Additionally, or alternatively, catheter 12 may include a strain relief body (not shown), which may be a part of hub portion 16 or may be separate from hub portion 16 to alleviate potential strain of kinking of elongated member 14 near its proximal end 15A.

Hub portion 16 may also include one or more access ports 17. Access ports 17 may be used to pass various components through or around elongated member 14. For example, access port 17 may permit the entry and advancement of wire 18 through inner lumen 25 that extends through elongated member 14. In other examples, one or more of access ports 17 may be connected directly to elongated member 14 separate of hub portion 16. In such examples, one or more of access ports 17 may be positioned distal to hub portion 16 but remain within the proximal portion of elongated member 14 that remains exterior to the patient during use.

FIGS. 1B and 1C provide greater detail of distal portion 22 of elongated member 14. Distal portion 22 includes tubular body 24. Tubular body 24 may define one or more body apertures 30 that extend through the sidewall of tubular body 24 permitting direct access to inner lumen 25. Body apertures 30 may expose secondary electrode 28 within inner lumen 25 to the fluid within the vessel of the patient. When in contact with a fluid within the vessel of a patient (e.g., blood or saline), body apertures 30 may provide an electrical pathway between primary electrodes 26 and secondary electrode 28 via the fluid. In such examples, both primary electrodes 26 and secondary electrode 28 will be exposed to the external environment of catheter 12 with the electrodes 26 and 28 being in fluid communication with the vessel wall of the patient. Energy source 20 may then be used to deliver an electrical signal (e.g., an electrical pulse) between primary and secondary electrodes 26 and 28 to induce cavitation of the fluid. The pressure pulse wave resulting from the cavitation procedure may be used to fracture or dislodge the calcified lesion present on or within the vessel wall.

In some examples, tubular body 24 may include one or more layers and configured to provide any desired shape and flexibility characteristics to elongated member 14. For example, tubular body 24 may include a multi-layer construction that includes an inner liner, one or more support structures (e.g., coils, braids, or the like), a shape member, an outer jacket, or combinations thereof.

Tubular body 24 may be constructed using any suitable materials. In some examples, tubular body 24 may be composed of one or more polymeric materials such as polyamide, polyimide, polyether block amide copolymer sold under the trademark PEBAX, polyethylene terephthalate (PET), polypropylene, aliphatic, polycarbonate-based thermoplastic polyurethane (e.g., CARBOTHANE), or a polyether ether ketone (PEEK) polymer that provides the desired flexibility. The polymeric materials may be non-electrically conductive and extruded as one or more tubes that are used to form the completed body of tubular body 24. If desired, a support structure or shape member may be included within tubular body 24 such as being disposed over or between one or more of the polymeric tubes used to form tubular body 24. The support structure or shape member may be used to impart the desired strength, flexibility, or geometric qualities to tubular body 24 and/or elongated member 14. The support structure or shape member may be formed using any suitable materials including, for example, metal or polymer-based wires used to form coils or braids, a hypotube, suitable shape memory materials such as nickel-titanium (nitinol), shape memory polymers, electro-active polymers, or the like. The support structure or shape member may be cut using a laser, electrical discharge machining (EDM), electrochemical grinding (ECG), or other suitable means to achieve a desired finished component length, apertures, and geometry. In some examples, the support structure or shape member may be arranged in a single or dual-layer configuration, and manufactured with a selected tension, compression, torque and pitch direction.

Primary electrodes 26 may be carried by tubular body 24 and may take on any suitable form. In some examples, primary electrodes 26 may define cylindrically shaped bodies that are secured (e.g., crimped) to tubular body 24. For example, primary electrodes 26 may be formed using a marker band crimped over tubular body 24. While primary electrodes 26 are primarily shown and described as being cylindrical in shape, other structures and shapes such as rings, ring or cylindrical segments, exposed segments of electrical conductors, wires, or support structures, or the like may also be used to form primary electrodes 26.

Primary electrodes 26 may be positioned at any appropriate interval and quantity along the length of distal portion 22 of elongated member 14. In some examples, primary electrodes 26 may be separated by a longitudinal distance of at least about 2 mm to about 5 mm from each other. Maintaining a separation difference of at least about 2 mm may allow primary electrodes 26 function independently of one another, where desired, such that the electrical signal does not pass from one primary electrode 26 to another.

Each of primary electrodes 26 may be positioned adjacent to one or more body apertures 30 to provide a pathway between a respective primary electrode 26 and wire 18 disposed within inner lumen 25. The separation distance between primary electrode 26 and a respective body aperture 30 along the longitudinal axis may determine whether the electrical pulse is delivered as an arc or corona. In examples in which an arc discharge is desired, a respective primary electrode 26 and a respective body aperture 30 may be separated by less than about 0.5 mm to establish an appropriate electrical connection between the respective primary electrode 26 and secondary electrode 28 through body aperture 30. In examples in which a corona discharge is desired, a respective primary electrode 26 and a respective body aperture 30 may be separated by the same distance (e.g., less than about 0.5 mm) or a much greater distance (e.g., separated by a distance of about 1 mm to about 5 mm). Additionally, or alternatively, body apertures 30 may aligned with a respective primary electrode 26 (e.g., the electrode configuration of FIG. 5A).

Primary electrodes 26 may be connected to energy source 20 via one or more electrical conductors 34 that extend along the length of elongated member 14 and electrically coupled to energy source 20 via one or more cables 35. In the example shown in FIGS. 1A-1C, primary electrodes 26 are connected in series by conductors 34. For example, conductors 34 may be formed using a single wire that is coupled (e.g., soldered) to each primary electrode 26 as the respective electrodes are coupled to tubular body 24. In such examples, each of primary electrodes 26 may be at the same electrical potential. However, in other examples, primary electrodes 26 may be connected to energy source 20 by individually activated conductors 34 or by using another suitable electrical arrangement.

In some examples, electrical conductors 34 and primary electrodes 26 may be imbedded or integrally formed with tubular body 24 such that electrical conductors 34 are secured between polymeric layers that make up part of tubular body 24. For example, as part of the construction of catheter 12, primary electrodes 26, electrical conductors 34, or both may be positioned over and secured to an inner layer of tubular body 24 using an outer layer (e.g., an outer jacket) of flexible polymeric material. In some examples, the outer layer may be heat shrunk on to the inner layer to form an exterior of elongated member 14 and secure electrical conductors 34 and primary electrodes 26 in place on elongated member 14. Portions of primary electrodes 26, if covered by the outer layer or material may then be removed by, for example, laser etching or other suitable technique to expose at least a portion each electrode 26 to the external environment so the exposed surface of the electrode contacts the surrounding fluid. In some examples, primary electrodes 26 may comprise an exposed surface area of less than about 0.1 mm$^2$.

Primary electrodes 26, wire 18, secondary electrode 28, conductors 34, or any other electrical conduit described herein may be formed using any suitable electrically conductive material including, for example, titanium alloys (e.g., Ti—Mo alloy), platinum or platinum-iridium alloys, stainless steel, copper, copper alloys (e.g., copper and hafnium or tungsten), tungsten, or the like. In some examples, conductors 34 or wire 18 may be formed using electrically insulated metal wires that extend along elongated member 14. The materials and design of primary electrodes 26, secondary electrode 28, wire 18, and conductors 34 may be selected such that the components do not significantly impede or hinder the navigability of catheter 12.

Wire 18 of catheter assembly 10 may be slidably disposed within inner lumen 25. In some examples, wire 18 may represent a guide wire such as a 0.014 inch gauge wire (e.g., about 0.36 mm OD). In some examples, wire 18 may include an electrically insulative sheath (e.g., made from paralyene, polyimide, PTFE, or the like) disposed over wire 18 such that only a portion of wire 18 is exposed to form secondary electrode 28. In the example illustrated in FIGS. 1A-1C, the exposed portion of wire 18 forming secondary electrode 28 occurs at the distal tip of wire 18, however in other examples, the exposed portion or portions of wire 18 may occur along other parts of wire 18. In some examples, wire 18 may exclude the presence of an electrically insulative sheath such that the entire body of wire 18 functions as secondary electrode 28. As described further below, the selection of the type of construction for wire 18 may depend on the type of cavitation procedure intended (e.g., corona-based cavitation or arc-based cavitation).

In some examples, distal portion 22 of elongated member 14 may also include an atraumatic, flexible tip 36 at distal end 15B of the elongated member 14. Flexible tip 36 can be affixed to the distal end of tubular body 24 via adhesive, crimping, over-molding, or other suitable techniques or may be integrally formed as part of tubular body 24. In some examples, flexible tip 36 can be made from a polymeric material (e.g., polyether block amide copolymer sold under the trademark PEBAX), a thermoplastic polyether urethane material (sold under the trademarks ELASTHANE or PELLETHANE), or other suitable materials having the desired properties, including a selected durometer.

Figure 2A:
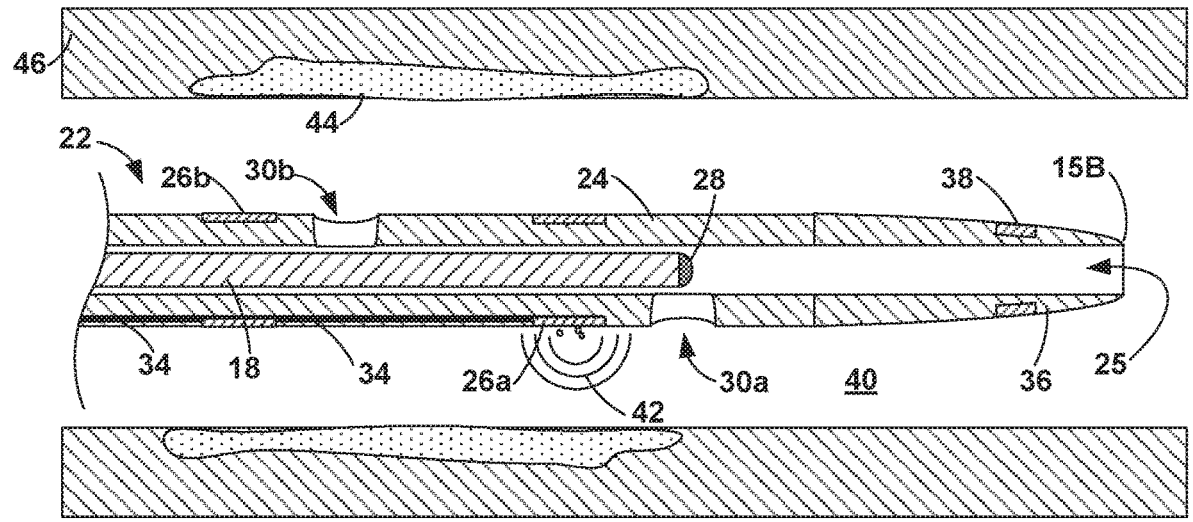
FIGS. 2A-2B are enlarged conceptual cross-sectional views of an example cavitation procedure that may be performed using the catheter assembly of FIGS. 1A-1C.
Figure 2B:
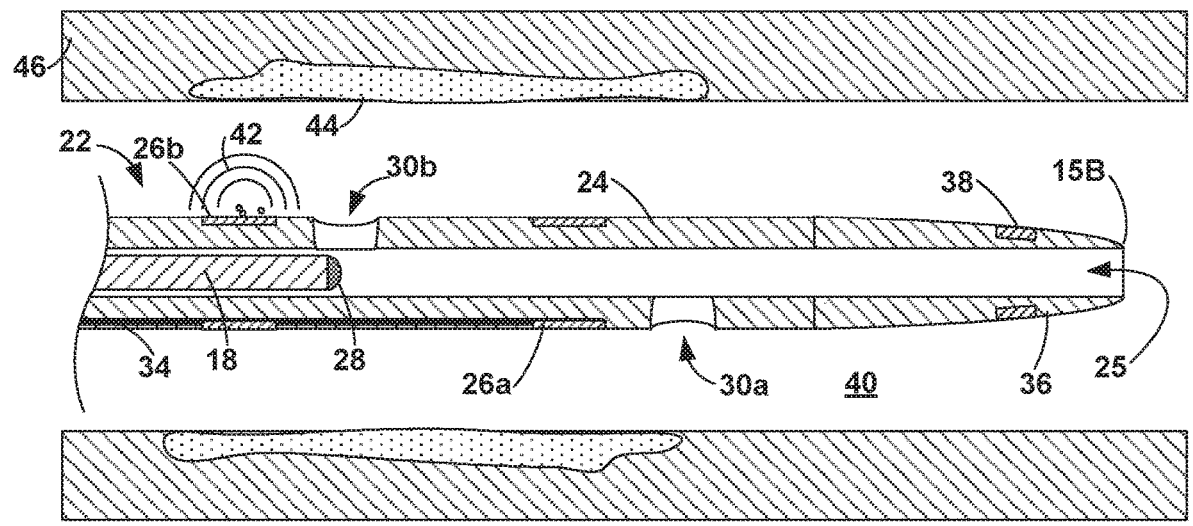
Figure 3:
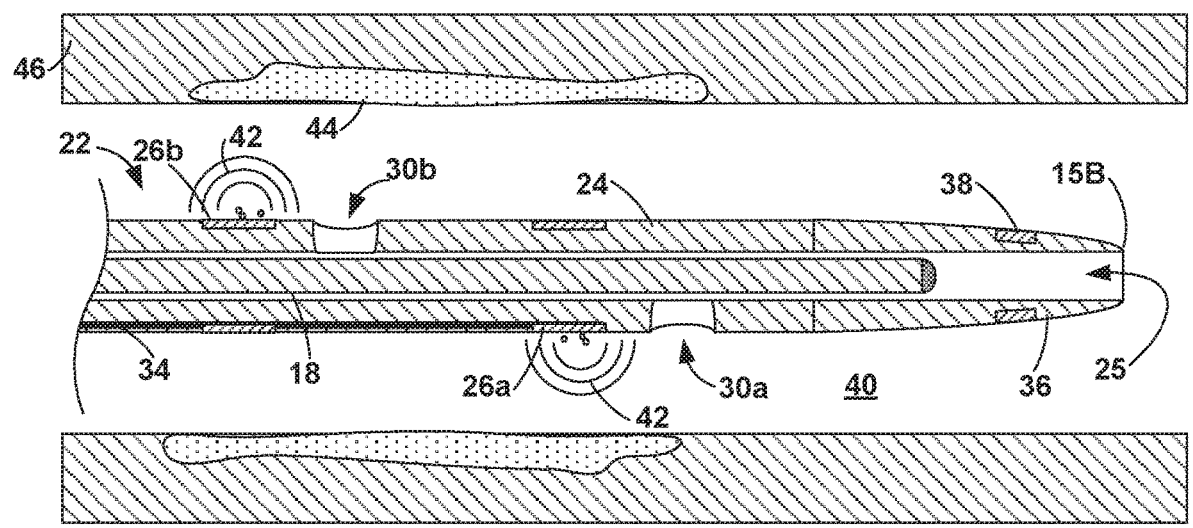
FIG. 3 is an enlarged conceptual cross-sectional view of another example cavitation procedure that may be performed using the catheter assembly of FIGS. 1A-1C.

FIGS. 2A, 2B, and 3 are enlarged conceptual cross-sectional views showing example cavitation procedures that may be performed using catheter assembly 10 of FIGS. 1A-1C. FIGS. 2A and 2B illustrate an example where cavitation is induced by individual primary electrodes 26, while FIG. 3 illustrates an example where cavitation is induced simultaneously using multiple primary electrodes 26.

FIG. 2A shows part of distal portion 22 of catheter 12 introduced to a target treatment site containing a calcified lesion 44 on or within a wall of vessel 46 of a patient. Wire 18 may be positioned within inner lumen 25 such that secondary electrode 28 is aligned with a first body aperture 30a, which is positioned adjacent to primary electrode 26a. In some examples, wire 18 may include visual markers along the proximal side, notches, rumble strips, radiopaque markers, or the like that help indicate the alignment of wire 18 relative to inner lumen 25.

Wire 18 may be covered with an electrically insulative material (e.g., sheath) so that only the distal tip of wire 18 is exposed to form secondary electrode 28. When secondary electrode 28 is aligned with first body aperture 30a, the presence of body aperture 30a will provide fluidic communication between primary electrode 26a and secondary electrode 28. Fluid 40 contained within or introduced into the vasculature of the patient (e.g., blood, contrast solution, saline, or the like) may fill body aperture 30a such that fluid 40 lies in direct contact with both primary electrode 26a and secondary electrode 28.

From the position shown in FIG. 2A, energy source 20 may deliver an electrical pulse in the form of a corona, arc, spark, or the like between primary electrode 26a and secondary electrode 28 using fluid 40 as the conductive medium. The electrical signal (e.g., arch or corona) causes fluid 40 to form gaseous steam/plasma bubbles within fluid 40 that form and cavitate near electrodes 26a and/or 28. The steam/plasma bubbles may represent relatively low-pressure pockets of vapor sourced by the surrounding fluid 40. The low-pressure steam/plasma bubbles eventually collapse in on themselves due to the relatively high pressure of the surrounding fluid 40 and heat loss of the steam/plasma bubbles to the surrounding fluid 40. As the steam/plasma bubbles collapse, the bubbles release a large amount of energy in the form of a high-energy pressure pulse wave 42 within fluid 40.

In some examples, the site for cavitation may be controlled by controlling the surface area and/or materials of exposed surfaces or primary and secondary electrodes 26 and 28. For example, when applying corona based cavitation, the electrode with the smaller surface area may have a higher current density and therefore act as the site for cavitation to occur. Additionally, or alternatively, the direction of the resultant pressure pulse waves produced by the cavitation may be controlled based on the circumferential orientation of the electrode where cavitation is to occur.

The formation and subsequent collapse of the steam/plasma bubbles may be short lived or nearly instantaneous, causing the pressure pulse waves 42 to originate near primary electrode 26a or secondary electrode 28. In some examples, the location where the steam/plasma bubbles originate may be controlled by reducing the amount of surface area exposed to fluid 40 on either primary electrode 26a or secondary electrode 28 provided for nucleation. In some examples, the steam/plasma bubbles will originate on the associated electrode 26a or 28 having the smallest exposed surface area. In some examples where the origination of the cavitation is desired near secondary electrode 28, the amount of secondary electrode 28 exposed may be controlled by controlling the size and/or number of body apertures 30*a* associated with the respective primary electrode 26*a*.

Once produced, pressure pulse waves 42 propagate through fluid 40 where they impact the wall of vessel 46 in which distal portion 22 is deployed, transmitting the mechanical energy of pressure pulse wave 42 into the tissue of vessel 46 and calcified lesion 44 at the target treatment site. The energy transmitted to calcified lesion 44 may cause the calcified lesion to fracture or break apart. In some examples, the relative intensity of pressure pulse waves 42 may be adjusted by controlling the intensity of the electrical signal delivered between primary electrodes 26 and secondary electrode 28. The intensity of the electrical signal may be a function of one or more of a voltage, a current, a frequency (e.g., a pulse rate in the case of pulses), a pulse width, or one or more other electrical signal parameters.

In some examples, fluid 40 may be introduced (e.g., perfused) into the vessel and body apertures 30 by the clinician. For example, elongated member 14 may be configured such that fluid 40, e.g., saline, contrast solution, or the like, may be introduced through inner lumen 25 via one or more supply tubes of catheter 12. In some examples, saline, as opposed to blood, may more readily undergo cavitation thereby requiring less energy to induce cavitation than blood when saline is used as fluid 40, however any suitable fluid 40 may be introduced into the vessel and body apertures 30 for the cavitation procedure. Example fluids 40 may include, but are not limited to, biocompatible fluids such as saline or similar solution with a salt content between about 0.9 weight percent (wt. %) and about 5 wt. %; contrast media (e.g., about 25 volume percent (vol. %) to about 75 vol. % contrast media), blood, or the like. The higher the salt content of the saline fluid, the higher the conductance will be for the fluid, thereby requiring less energy to increase the temperature of the fluid and induce cavitation. Additionally, the higher the concentration of contrast media, the more viscous fluid 40 will be leading to a higher dissipation of the cavitation bubbles.

After performing cavitation using primary electrode 26*a*, wire 18 or catheter 12 may be retracted proximally relative to calcified lesion 36 until secondary electrode 28 aligns with a second body aperture 30*b* adjacent to a second primary electrode 26*b* (e.g., FIG. 2B). Energy source 20 may then deliver another electrical pulse which travels between primary electrode 26*b* and secondary electrode 28 to cause fluid 40 in contact with both primary and secondary electrodes 26*b* and 28 to undergo cavitation and produce a pressure pulse wave 42 as described above. Depending on the orientation (e.g., annular position around tubular body 24) and size of body apertures 30 or the exposed surface of primary electrodes 26, the resulting pressure pulse wave 42 may be directed to the same or different radial positions along a wall of vessel 46.

The above process may be continued for additional primary electrodes 26 positioned along elongated member 14 until a desired amount of pulse wave energy has been delivered into vessel 46 and calcified lesion 44 over a desired portion of the vessel wall.

FIG. 3 illustrates another example cavitation procedure that may be performed using catheter 12. FIG. 3 shows part of distal portion 22 of catheter 12 introduced to a target treatment site containing calcified lesion 44 on or within a wall of vessel 46 of the patient. Wire 18 may be positioned within inner lumen 25, however unlike the example of FIGS. 2A and 2B, wire 18 may exclude the presence of an electrically insulative sheath such that the entire body of wire 18 effectively functions as a secondary electrode where wire 18 is exposed to fluid 40 by body apertures 30*a* and 30*b*.

Energy source 20 may deliver an electrical pulse which travels between each of primary electrodes 26*a* and 26*b* and wire 18 (e.g., the secondary electrode) to cause fluid 40 in contact with both primary electrodes 26*a* and 26*b* and wire 18 via body apertures 30*a* and 30*b* to undergo cavitation and produce pressure pulse waves 42 as described above. In some examples, the electrical signal delivered between primary electrodes 26*a* and 26*b* and wire 18 may be characterized as a corona. The exposed surfaces of primary electrodes 26*a* and 26*b* and/or location of body apertures 30 may be oriented in different circumferential directions alone elongated member 14 to allow for 360° deployment of the pressure pulse waves within the vessel.

By conducting the above cavitation procedures in vessel 46 of a patient within fluid 40 in direct and intimate contact with a wall of vessel 46, the transfer of energy from pressure pulse waves 42 to the target calcified lesion 44 may be more efficient as compared to a cavitation procedure that introduces one or more intermediate devices, such as a balloon, between the source of cavitation (e.g., primary electrodes 26) and calcified lesion 44. Additionally, by including a plurality of primary electrodes 26, a plurality of body apertures 30, or both, the techniques of this disclosure may allow for the pressure pulse wave energy to be delivered over a longer longitudinal distance of vessel 46 without needing to reposition distal portion 22 within vessel 46 mid process.

In some examples, the more efficient transfer of energy from pressure pulse waves 42 to calcified lesion 44 may reduce the duration of which the cavitation procedure is performed or reduce the energy requirements needed to sufficiently fracture or break apart calcified lesion 44 resulting in an overall shorter procedure. Additionally, or alternatively, due to the improved efficiency of the cavitation process, the cross-sectional profile of catheter 12 may be reduced. For example, the lower power requirements may mean that the components used in the cavitation process (e.g., primary electrodes 26, wire 18, and the like) may require a lower energy load thereby allowing for smaller gauge of components to be incorporated into catheter 12. In some examples, the lowered power demands may also permit catheter 12 and associate energy source 20 to be operated as a handheld unit.

Following completion of either of the above described cavitation processes, vessel 46 may be subsequently expanded (e.g., via balloon expansion) to a larger flow diameter. For instance, the clinician may position a balloon (e.g., a POBA) adjacent to the location of cavitation and expand the balloon (e.g., to about 4-6 atmospheres of pressure). In some examples, the cavitation process and balloon expansion sequence may be performed once or may be performed multiple times.

Figure 4:
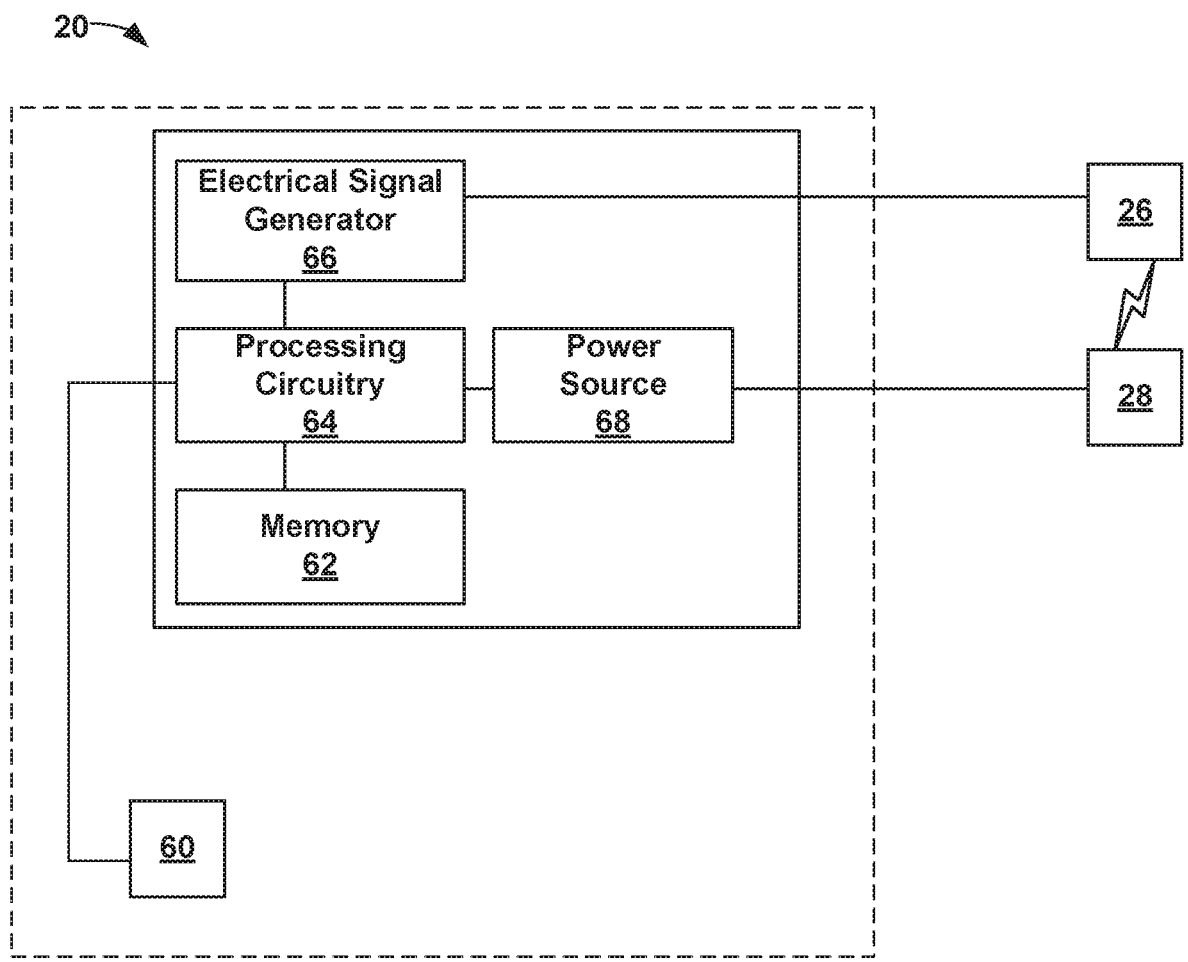
FIG. 4 is a schematic block diagram of an example energy source that may be used with the catheters described herein to induce cavitation of a fluid.

FIG. 4 is a schematic block diagram of an example energy source 20 that may be used with catheter assembly 10 of FIG. 1 to induce cavitation of fluid 40. FIG. 4 shows a schematic block diagram of an example energy source 20 that may be used with catheter assembly 10 to induce cavitation within fluid 40. Energy source 20 includes control mechanism 60, memory 62, processing circuitry 64, electrical signal generator 66, and power source 68.

Processing circuitry 64 may include any one or more microprocessors, controllers, digital signal processors (DSPs), application specific integrated circuits (ASICs), field-programmable gate arrays (FPGAs), discrete logic circuitry, or any processing circuitry configured to perform the features attributed to processing circuitry 64. The functions attributed to processors described herein, including processing circuitry 64, may be provided by a hardware device and embodied as software, firmware, hardware, or any combination thereof. In some examples, processing circuitry may include instructions to recognize a particular primary and secondary electrode 26 and 28 configuration or allow a clinician to manually input the specific primary and secondary electrode 26 and 28 configuration of catheter 12. In some examples, energy source 20 may include additional components such as, a display device or user input device that are not expressly shown for displaying information from processing circuitry 64 or allowing the clinician to input information.

Memory 62 may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processing circuitry 64, cause processing circuitry 64 to perform various functions described herein. Memory 62 may be considered, in some examples, a non-transitory computer-readable storage medium including instructions that cause one or more processors, such as, e.g., processing circuitry 64, to implement one or more of the example techniques described in this disclosure. The term "non-transitory" may indicate that the storage medium is not embodied in a carrier wave or a propagated signal. However, the term "non-transitory" should not be interpreted to mean that memory 62 is non-movable. As one example, memory 62 may be removed from energy source 20, and moved to another device. In certain examples, a non-transitory storage medium may store data that can, over time, change (e.g., in RAM).

Processing circuitry 64 is configured to control energy source 20 and electrical signal generator 66 to generate and deliver the electrical signal across one or more primary and secondary electrodes 26 and 28 to induce cavitation of fluid 40. Electrical signal generator 66 includes electrical signal generation circuitry and is configured to generate and deliver an electrical signal in the form of and electrical pulse. In the case of electrical pulses, electrical signal generator 66 may be configured to generate and deliver pulses having an amplitude of about 500 volts (V) to about 5000 V (e.g., between about 1500V to about 3000 V), a pulse width of about 1 microsecond (μs) to about 5 μs for arc-type cavitation or about 10 μs to about 200 μs for corona-type cavitation, and a frequency of about 0.5 Hertz (Hz) to about 5 Hz. In some examples, catheter 12 may be configured such that electrical conductors 34 are independently coupled to one or more primary electrodes 26. In such examples, processing circuitry 64 may control electrical signal generator 66 to generate and deliver multiple electrical signals via different combinations of electrical conductors 34 and/or primary electrodes 26. In these examples, energy source 20 may include a switching circuitry to switch the delivery of the electrical signal using primary electrodes 26, e.g., in response to control by processing circuitry 64.

Power source 68 delivers operating power to various components of energy source 20. In some examples, power source 68 may represent hard-wired electrical supply of alternating or direct electrical current. In other examples, power source 68 may include a small rechargeable or non-rechargeable battery and a power generation circuit to produce the operating power. Recharging may be accomplished through proximal inductive interaction between an external charger and an inductive charging coil within energy source 20.

A control mechanism 60, such as foot pedal, handheld, or remote-control device, may be connected to energy source 20 to allow the clinician to initiate, terminate and, optionally, adjust various operational characteristics of energy source 20, including, but not limited to, power delivery. Control mechanism 60 can be positioned in a sterile field and operably coupled to the energy source 20 and can be configured to allow the clinician to selectively activate and deactivate the energy delivered to one or more of primary and secondary electrodes 26 and 28. In other embodiments, control mechanism 60 may be built into hub portion 16.

Figure 5A:
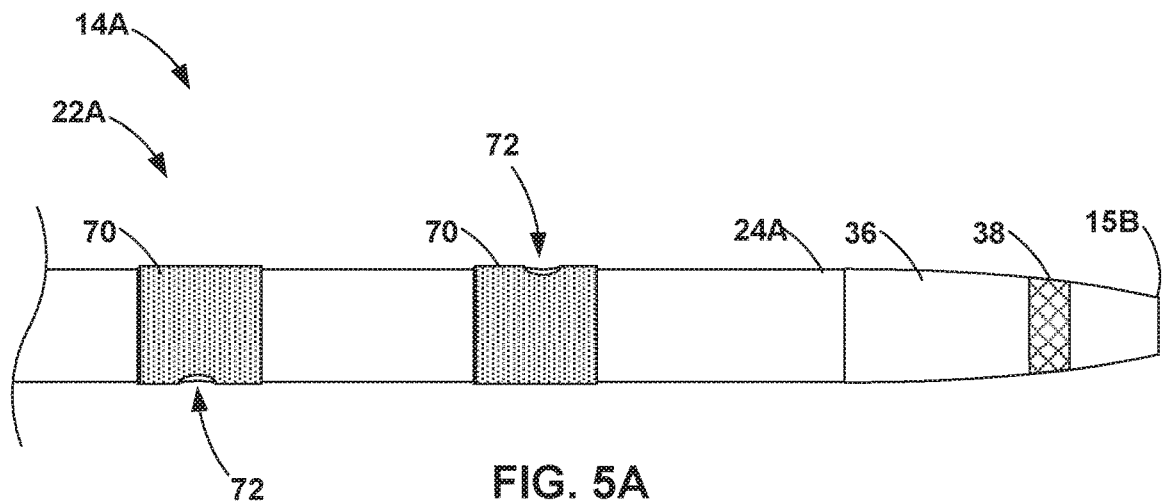
FIGS. 5A and 5B are schematic side views of an example electrode configuration that may be used with the catheters described herein.
Figure 5B:
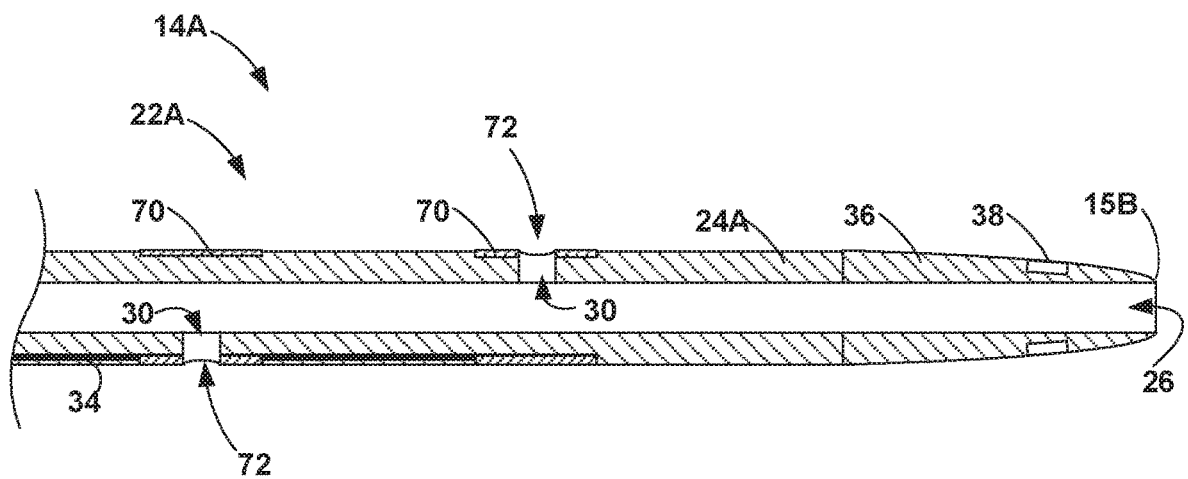

FIGS. 5A-6B illustrate additional schematic side views of example electrode configurations that may be used with catheter assembly 10 or the other catheter assemblies described herein. FIGS. 5A and 5B are schematic diagrams illustrating both a side view (FIG. 5A) and a cross-sectional side view (FIG. 5B) of an example distal portion 22A of an elongated member 14A that may be used with catheter 12 or the other catheters described herein. Distal portion 22A includes a tubular body 24A that defines a plurality of body apertures 30 that extend through a sidewall of tubular body 24A. Elongated member 14A also includes one or more primary electrodes 70 carried along tubular body 24 (e.g., carried over an electrically insulative inner layer). Primary electrodes 70 may be substantially similar to primary electrodes 26 described above, however each of primary electrodes 70 may further define an electrode aperture 72 extending through the body of the electrode. Each electrode aperture 72 may be substantially aligned (e.g., aligned or nearly aligned) with a respective body aperture 30 such that the two apertures form a single opening (e.g., the two apertures are concentric or coaxial to with one another). In this configuration, the pathway between primary electrodes 70 and secondary electrode 28 may be created directly through each of primary electrodes 70 with portions of tubular body 24A separating the two electrodes from being in direct contact.

In some examples, both electrode apertures 72 and body apertures may be formed at the same time using laser etching or other suitable technique to form the respective apertures after primary electrodes 70 have been added to distal portion 22A. Additionally, or alternatively, the formation of electrode apertures 72 may produce the exposed surface of primary electrodes 70 used in the cavitation procedures. For example, an outer jacket may be formed over primary electrodes 70 as part of the formation of tubular body 24A. The ablation process used to create electrode apertures 72 may simultaneously remove part of the outer jacket covering primary electrodes 70, thereby exposing the surface of primary electrode 70 along the edge of electrode aperture 72. In some examples, electrode apertures 72 may define an aperture diameter on between about 75 μm and about 200 μm.

In some examples, by constructing primary electrodes 70 with corresponding electrode apertures 72, the location and orientation of the resulting pressure pulse waves 42 generated during a cavitation procedure may be controlled by controlling the location and direction of electrode apertures 72. Furthermore, the relatively short distance between a respective primary electrode 70 and secondary electrode 28 when wire 18 is aligned within lumen 25 (e.g., less than about 75 μm such as less than about 50 μm) may help ensure that the electrical signal is delivered across only a particular set of primary and secondary electrodes to cause fluid 40 to cavitate.

Figure 6A:
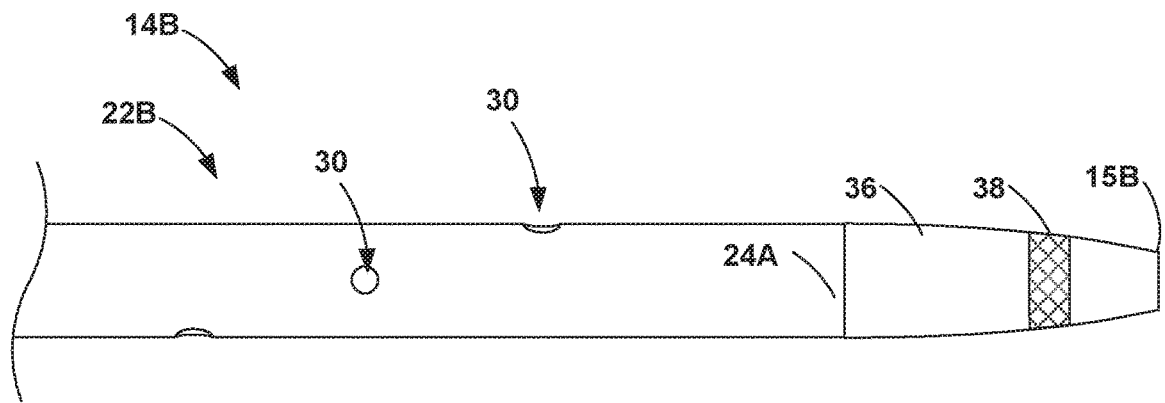
FIGS. 6A and 6B are schematic side views of an example electrode configuration that may be used with the catheters described herein.
showing various interactions between the primary electrodes and the secondary electrode.
Figure 6B:
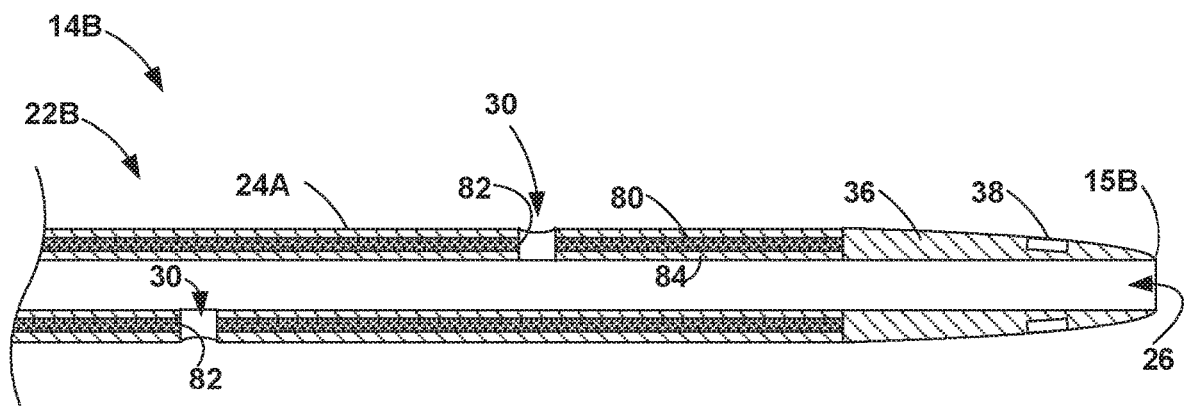

FIGS. 6A and 6B are schematic diagrams illustrating both a side view (FIG. 6A) and a cross-sectional side view (FIG. 6B) of another example distal portion 22B of an elongated member 14B that may be used with catheter 12 or the other catheters described herein. Distal portion 22B includes a tubular body 24B that defines a plurality of body apertures 30 that extend through a sidewall of tubular body 24B. Tubular body includes an electrically conductive support structure 80 such as a metallic braid, coil, hypotube, shape member, or the like. Support structure 80 may provide structural support, shape memory properties, or the like to elongated member 14B as well as serve as an electrical conductor (e.g., electrical conductor 34 of FIGS. 1A-1C) for the primary electrodes. Body apertures 30 may pass directly through support structure 80 to expose portions of support structure 80 to the surrounding fluid 40 (e.g., the external environment of catheter 12). The exposed portions of support structure 80 may be characterized as primary electrodes 82 and may perform substantially the same function as the exposed portions of primary electrodes 26 described above. In some such examples, tubular body 24B may include an inner liner 84 of a non-conductive material that may be used to separate primary electrodes 82 from wire 18 and/or secondary electrode 28 contained within inner lumen 25 of tubular body 24B.

Figure 7A:
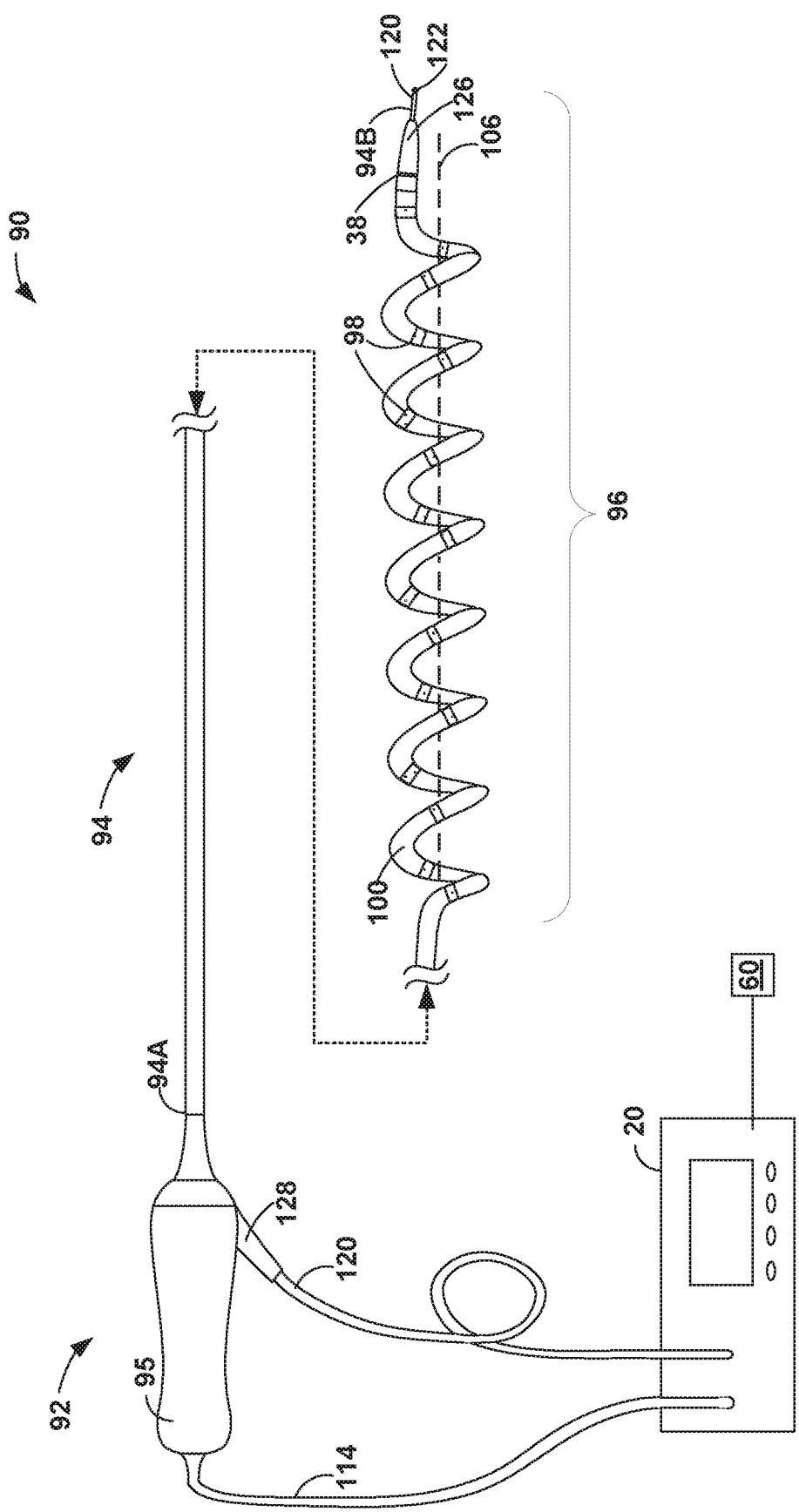
FIG. 7A is a schematic side view of another example catheter assembly that includes a catheter comprising an elongated member and a hub portion, and an energy source electrically coupled to the catheter.
Figure 7B:
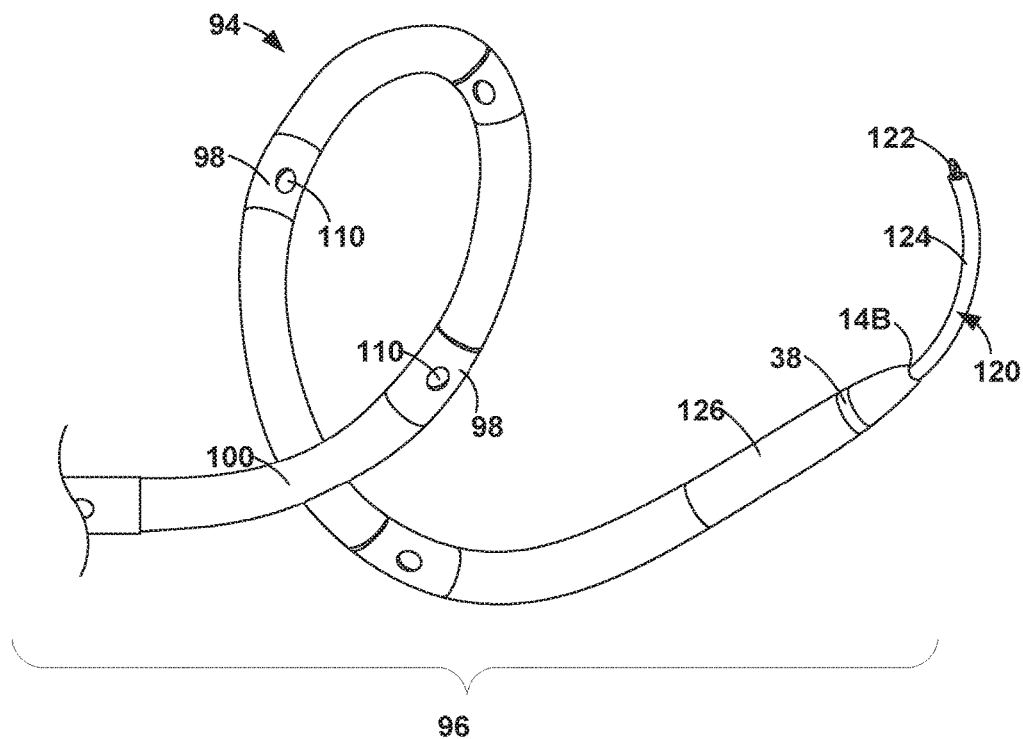
FIG. 7B is a perspective view of the distal portion of the catheter of FIG. 7A.
Figure 7C:
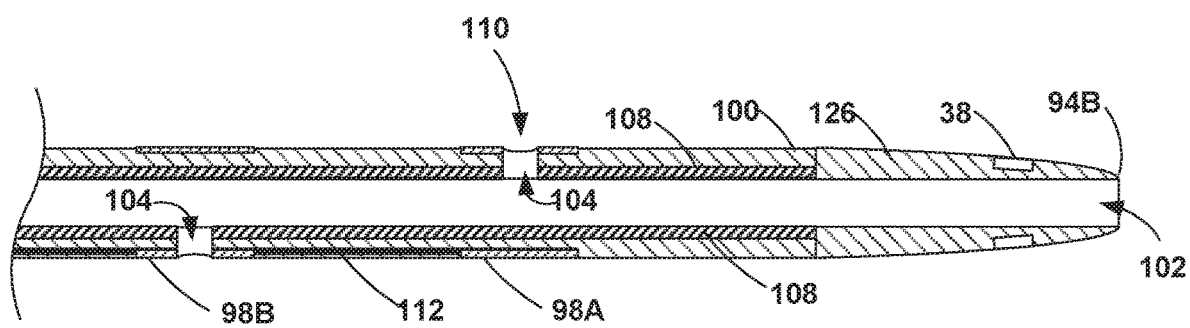
FIG. 7C is a cross-sectional side view of the distal portion of the catheter of FIG. 7A in a linear profile.

In some examples, elongated member 14 of catheter 12 may include a distal portion configured to transform from a collapsed, low-profile (e.g., linear) configuration to a deployed curvilinear configuration (e.g., helical or spiral configuration) when positioned adjacent the target treatment site. FIG. 7A-7C are schematic views of another example catheter assembly 90, which includes a catheter 92 comprising an elongated member 94 and a hub portion 95, and an energy source 20 electrically coupled to catheter 92. Elongated member 94 extends from a proximal end 94A to a distal end 94B with proximal end 94A connected to hub portion 95. Elongated member 94 includes a distal portion 96 comprising a plurality of primary electrodes 98 positioned along tubular body 100. Distal portion 96 is configured to transform into a curvilinear configuration (e.g., helical or spiral shaped) when deployed within vasculature of a patient. Energy source 20 is configured to deliver electrical energy to primary electrodes 98 to induce cavitation of a fluid within a vessel of the patient to deliver therapy to a calcified lesion on or within the vessel wall using a pressure pulse wave created by the cavitation of the fluid.

FIGS. 7B and 7C provide greater detail of distal portion 96 of catheter 92. FIG. 7B is a schematic perspective view of distal portion 96 and FIG. C is a cross-sectional side view of distal portion 96. For ease of illustration and description, FIG. 7C is shown with distal portion 96 having a linear profile where elongated member 94 is extended linearly rather than in the curvilinear configuration as shown in FIGS. 7A and 7B.

One or more aspects of catheter assembly 90 and catheter 92 may be substantially similar to the systems described above with respect to FIGS. 1-6 including, for example, the configuration of the primary electrodes, parts of the tubular body, the hub portion, the body and/or electrode apertures, the cavitation processes preformed, or the like apart from any differences noted below. For simplicity, catheter 92 will be primarily described as having primary electrodes 98 configuration similar primary electrodes 70 described in FIGS. 6A and 6B, however other electrode configurations and designs described herein may also be incorporated into the curvilinear construction of catheter 92.

Distal portion 96 of elongated member 94 includes a tubular body 100 defining an inner lumen 102 and a plurality of body apertures 104 that extend through a sidewall of tubular body 100 into the inner lumen 102. Tubular body 100 is configured to change from a first collapsed configuration (e.g., low-profile or generally linear configuration) to a second curvilinear configuration. The curvilinear configuration may define a spiral or helically-shaped configuration such that distal portion 96 of elongated member 94 curls (e.g., helically wraps) about a central longitudinal axis 106.

In some examples, the deployed curvilinear configuration of distal portion 96 may be established using a shape member 108 comprising a shape memory metal or other material. Shape member 108 may be used to provide a spiral/helical-shape to the relatively flexible distal portion 96 of catheter 92. In some examples, shape member 108 may be formed within or as part of tubular body 100. For example, tubular body 100 may be composed of one or more layers of polymeric materials such as polyamide, polyimide, polyether block amide copolymer sold under the trademark PEBAX, polyethylene terephthalate (PET), polypropylene, aliphatic, polycarbonate-based thermoplastic polyurethane (e.g., CARBOTHANE), or a polyether ether ketone (PEEK) polymer that provides the desired flexibility. The polymeric materials may be extruded as one or more tubes that are used to form the completed body of tubular body 100. Shape member 108 may be disposed over or between one or more of the polymeric tubes used to form tubular body 100 using suitable techniques to impart the desired geometric qualities to tubular body 100.

Shape member 108 may be formed from suitable shape memory materials such as nickel-titanium (nitinol), shape memory polymers, electro-active polymers, or the like that are pre-formed or pre-shaped into the desired curvilinear geometry. In some examples, shape member 108 may include a tubular structure such as multifilar stranded wire (e.g., Helical Hollow Strand™ sold by Fort Wayne Metals of Fort Wayne, Ind.) comprising nitinol or other shape memory material. Shape member 108 may be cut using a laser, electrical discharge machining (EDM), electrochemical grinding (ECG), or other suitable means to achieve a desired finished component length, apertures, and geometry for creating the curvilinear configuration. In some examples, shape member 108 may be formed from a variety of different types of materials, arranged in a single or dual-layer configuration, and manufactured with a selected tension, compression, torque and pitch direction.

In some examples, the curvilinear configuration may be characterized by dimensions of the curved shape (e.g., the shape of the helix) that are distinct from the dimensions of tubular body 100 or components thereof. In some examples, the curvilinear configuration may define a diameter (e.g., helix diameter) of about 1 mm to about 30 mm and a pitch (e.g., distance along longitudinal axis 106 for one full rotation) of about 0.5 mm to about 5 mm. Additionally, or alternatively, the pitch or diameter of the curvilinear configuration may be expressed as a ratio compared to the diameter of tubular body 100. In some examples, the diameter of the curvilinear configuration to the diameter of tubular body 100 may be about 2:1 to about 30:1 but other ratios may also be used.

As shown in FIGS. 7A and 7B, tubular body 100 may be configured to exhibit pre-set spiral/helical configuration that defines the deployed state of the catheter assembly 90 such that plurality of primary electrodes 98 are offset both angularly and longitudinally from each other when in the deployed curvilinear configuration thereby allowing primary electrodes 98 to engage with the vessel wall of a patient at different parts and radial position of even though the relative diameter of tubular body 100 may be less than that of the vessel. In some examples, the curvilinear configuration may position tubular body 100 and primary electrodes 98 in intimate contact or with little or no space between the exterior surfaces of elongated member 94 and the interior surface of the vessel wall.

In some examples, primary electrodes 98 may define cylindrically shaped bodies that are positioned over and secured (e.g., crimped) to tubular body 100. While primary electrodes 98 are primarily shown and described as being cylindrical in shape, other structures and shapes such as rings, ring or cylindrical segments, or the like may be used. Additionally, or alternatively, primary electrodes 98 may be formed by exposed segments of an electrical conductor, a support structure, shape member 108, or the like.

Plurality of primary electrodes 98 may be carried by tubular body 100 and may define a surface area exposed to fluid 40. In some examples, each of primary electrodes 98 may define a corresponding electrode aperture 110 that extends through the respective electrode 98 (e.g., similar to electrode apertures 72). Each electrode aperture 110 may aligned with a corresponding body aperture 104 of tubular body 100 to provide direct access (e.g., provide fluid communication) between inner lumen 102 and exposed surfaces of primary electrodes 98.

At least a portion of each of primary electrodes 98 lies in direct contact with the fluid (e.g., blood or saline) in vasculature of the patient. For example, at least some of the surface of each primary electrode 98 adjacent to or at the edge where electrode aperture 110 is formed, is expose to the external environment of catheter 92. In some examples, at least a portion of each primary electrode 98 forms an exterior surface of elongated member 94 and catheter 92.

Primary electrodes 98 may be connected to energy source 20 via one or more electrical conductors 112 that extend along the length of elongated member 94 and electrically coupled to energy source 20 via one or more cables 114. As described above, in some examples, electrical conductors 112 may connect primary electrodes in series using, for example, a single wire coupled (e.g., soldered) to each of primary electrodes 98. In such examples, each of primary electrodes 98 may be at the same electrical potential.

In some examples, one or more of electrical conductors 112, primary electrodes 98, and shape member 108 may be integrally formed with tubular body 100. For example, as part of the construction of catheter 92, primary electrodes 98 and electrical conductors 112 may be positioned over and secured to shape member 108 using a layer (e.g., outer jacket) of flexible polymeric material. The layer may be heat shrunk onto shape member 108 help secure electrical conductors 112 and primary electrodes in place relative to the shape member 108. Electrode apertures 110 may then be formed or opened via laser etching or other suitable technique to expose at least a portion each electrode 98 to the external environment. In some examples, one or more additional layers of polymeric material may be positioned between shape member 108 and primary electrodes 98 and/or conductors 112 or positioned under shape member 108 to further electrically isolate shape member 108 from other components of catheter assembly 90.

Catheter assembly 90 also includes a wire 120 that includes a secondary electrode 28 that functions as the return pathway to energy source 20. Wire 120 may be substantially similar to wire 18 described above. In some examples, wire 120 may be disposed within inner lumen 102 and slidably transitioned to align secondary electrode 122 with a respective primary electrode 98. As described above, wire 120 may include an electrically insulative sheath 124 (e.g., made from paralyene, polyimide, PTFE) disposed over wire 120 such that only a portion of wire 120 is exposed and forms secondary electrode 122. In the example illustrated in FIGS. 7A-7C, the exposed portion of wire 120 forming secondary electrode 122 is indicated at the distal tip of wire 120, however in other examples, the exposed portion of wire 120 may occur along other parts of wire 120 or the entire wire 120 may be exposed.

During use, wire 120 may be slidably maneuvered within inner lumen 102 to align secondary electrode 122 with an electrode aperture 110 of a respective primary electrode 98. Due to the presence of electrode aperture 110 and body aperture 104, the respective primary electrode 98 and secondary electrode 122 will be in direct contact with the fluid contained in the vessel of the patient. Upon alignment, a relatively high voltage electrical signal may be transmitted via energy source 20, between secondary electrode 122 and the adjacent primary electrode 98 to induce cavitation of the fluid in direct contact with both secondary electrode 122 and the adjacent primary electrode 98. The cavitation of the fluid may deliver resulting pressure shock wave that propagates through the fluid and impacts the vessel wall of the patient to fracture or dislodge a calcified lesion present on or within the vessel wall.

Catheter 92 may also include an atraumatic, flexible tip 126 at distal end 94B of the elongated member 94. In some examples, flexible tip 126 may be curved and configured to direct wire 120 away from the vessel wall when catheter 92 is in the pre-set deployed configuration. This feature may help facilitate alignment of the deployed curvilinear (e.g., helical) configuration in the vessel as it expands, while also reducing the risk of injuring the blood vessel wall when the distal tip of wire 120 is advanced from distal end 94B. The curvature of the tip 126 can be varied depending upon the particular sizing/configuration of the curvilinear configuration. For example, tip 126 may be curved such that it is off the pre-set spiral/helical axis (axis 106) defined by shape member 108. Flexible tip 126 can be affixed to the distal end of tubular body 100 via adhesive, crimping, over-molding, or other suitable techniques or may be integrally formed as part of tubular body 100.

Hub portion 95 may be substantially similar to hub portion 16 described above and may include one or more luers or other mechanisms (e.g., access ports 128) for establishing connections between catheter 92 and other devices. Access ports 128 may be used to pass various components through or around elongated member 94. For example, access port 128 may permit the entry and advancement of wire 120 through inner lumen 102 that extends through elongated member 94. In other examples, one or more of access ports 128 may be connected directly to elongated member 94 separate of hub portion 95.

The curvilinear design of elongated member 94 may allow for plurality of primary electrodes 98 to be positioned in closer proximity (e.g., direct or near direct contact) to the vessel wall of the patient allowing for a higher concentration of energy from the pressure pulse waves to be delivered into the vessel wall due to the close proximity between the source of cavitation and the vessel wall, as opposed to other catheter designs that may otherwise position the electrodes closer to a central longitudinal axis of vessel as opposed to adjacent to the vessel walls.

Figure 8A:
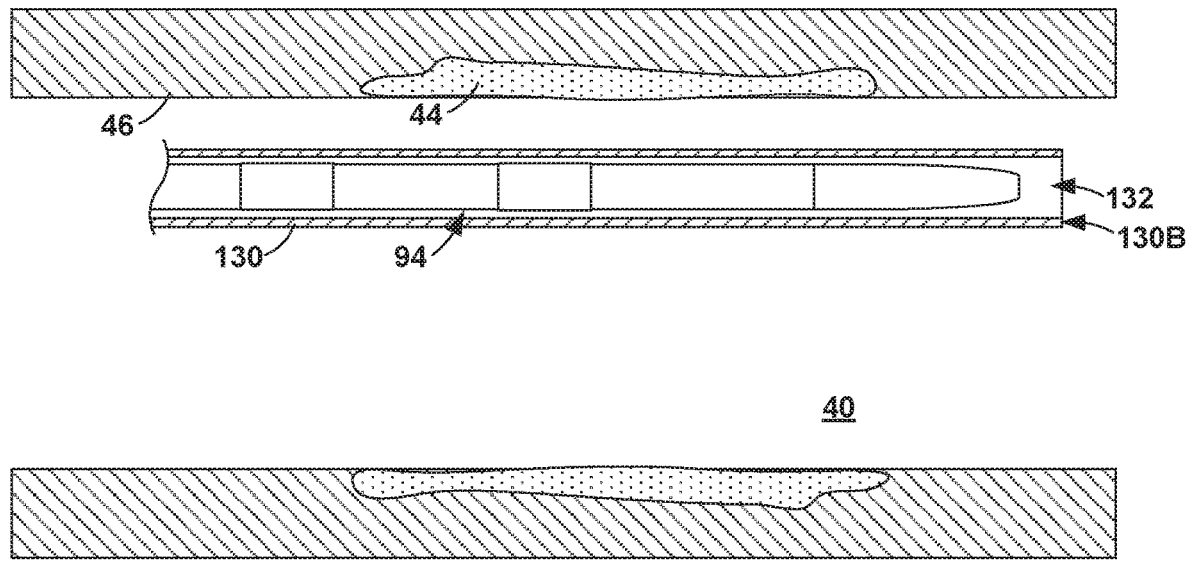
FIGS. 8A and 8B are enlarged conceptual side views of the distal portion of the catheter of FIG. 7A illustrating one example technique for introducing the distal portion through vasculature of a patient using a delivery sheath to help guide the elongated member to a target treatment site.
Figure 8B:
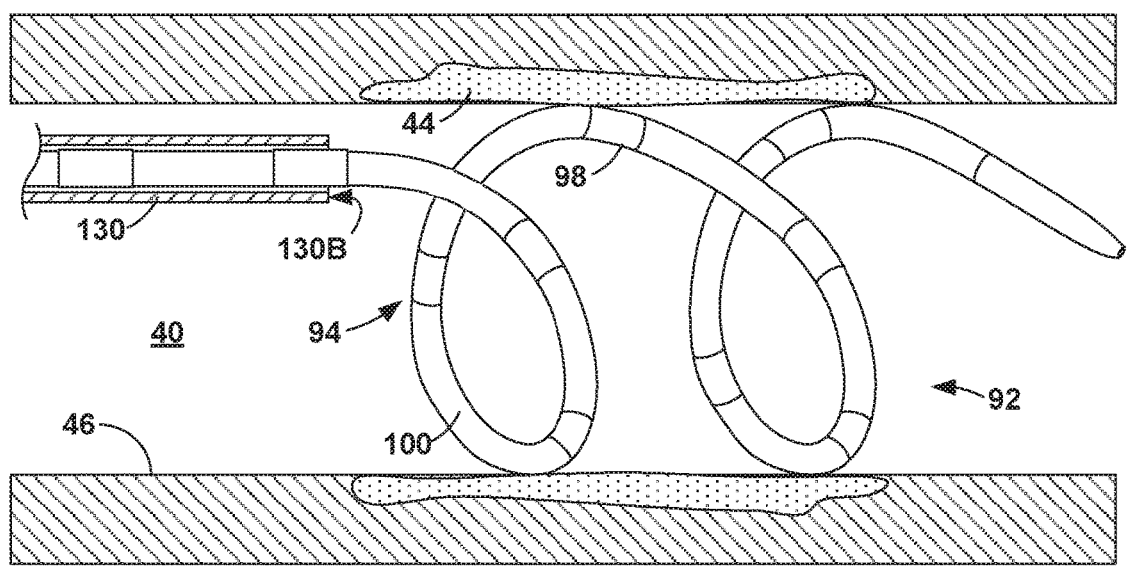

Distal portion 96 of elongated member 94 may be introduced through vasculature of a patient using any suitable technique. FIGS. 8A and 8B are an enlarged conceptual side views of distal portion 96 illustrating one example technique using a delivery sheath 130 to help guide elongated member 94 through vasculature of a patient to a target treatment site that contains a calcified lesion 44 on or within a wall of vessel 46. As shown in FIG. 8A, elongated member 94 may be positioned within an inner lumen 132 of delivery sheath 130. The body of delivery sheath 130 may maintain elongated member 94 in a collapsed configuration (e.g., low-profile or linearly extended). In some examples, delivery sheath 130 may be configured to maintain elongated member 94 in the collapsed configuration while also providing sufficiently flexibility to facilitate navigation through tortuous vasculature of a patient.

Once adjacent to the target treatment site, delivery sheath 130 may be withdrawn proximally from distal portion 96 of elongated member 94 to allow distal portion 96 to advance past distal end 130B and transition into the curvilinear configuration (e.g., FIG. 8B). Absent the structural constraints of delivery sheath 130, distal portion 96 may freely transition to the deployed, curvilinear configuration such as a helical or spiral shape, where elongated member 94 including tubular body 100 and primary electrodes 98 are positioned in close or direct contact with vessel 46. In order to retrieve catheter 92, delivery sheath 130 may be slid distally relative to elongated member 94 to allow distal portion 96 to transition back into the low profile or collapsed configuration within lumen 132. In some examples, the interior surface delivery sheath 130 may include lubricating coating, such as a hydrophilic coating, to help slidably advance distal portion 96 within inner lumen 132 of delivery sheath 130. Example materials for constructing delivery sheath 130 may include, for example, polyethylene (e.g., HDPE or LDPE), polyamide, or the like.

In some examples, delivery sheath 130 may be included as part of catheter assembly 90. For example, delivery sheath 130 may form part catheter 92 disposed over tubular body 100 and configured to be retracted proximally by the clinician once both elongated member 94 and delivery sheath 130 have been advanced towards the target treatment site. In some such examples, both elongated member 94 and delivery sheath 130 may be simultaneously navigated through the tortuous vasculature of the patient. In other examples, delivery sheath 130 may represent a delivery catheter that is initially advanced through vasculature of the patient to the target treatment site followed by introduction and advancement of distal portion 96 of elongated member 94 through inner lumen 132 of delivery sheath 130.

In other examples, distal portion 96 may be navigated through vasculature of a patient using wire 120. For example, wire 120 may include relatively stiff proximal portion and a relatively flexible distal portion. Wire 120 may be initially navigated through vasculature of the patient until the distal end of wire 120 is positioned within proximity of the target treatment site. Elongated member 94 may then be advanced over wire 120. The relatively stiff configuration of the proximal portion of wire 120 may help maintain distal portion 96 of elongated member 94 in the low-profile or collapsed configuration by exerting a biasing force that overcomes force of shape member 108 to transition into the deployed curvilinear configuration. As distal end 94B of elongated member 94 approaches the distal portion of wire 120, the increased flexibility of wire 120 may be insufficient to maintain distal portion 96 of elongated member 94 in the low profile or collapsed configuration, thereby allowing distal portion 22 to transition into the deployed curvilinear configuration. For example, tubular body 100 may comprise a shape-recovery force sufficient to overcome a straightening force provided by the distal portion of wire 120 to transform distal portion 96 of elongated member 94 to the curvilinear configuration when the distal end of wire 120 is aligned or proximal to distal end 94B of elongated member 94. In order to retrieve catheter 92, wire 120 may be slid distally relative to elongated member 94 to allow distal portion 96 to transition back into the low profile or collapsed configuration.

Figure 9A:
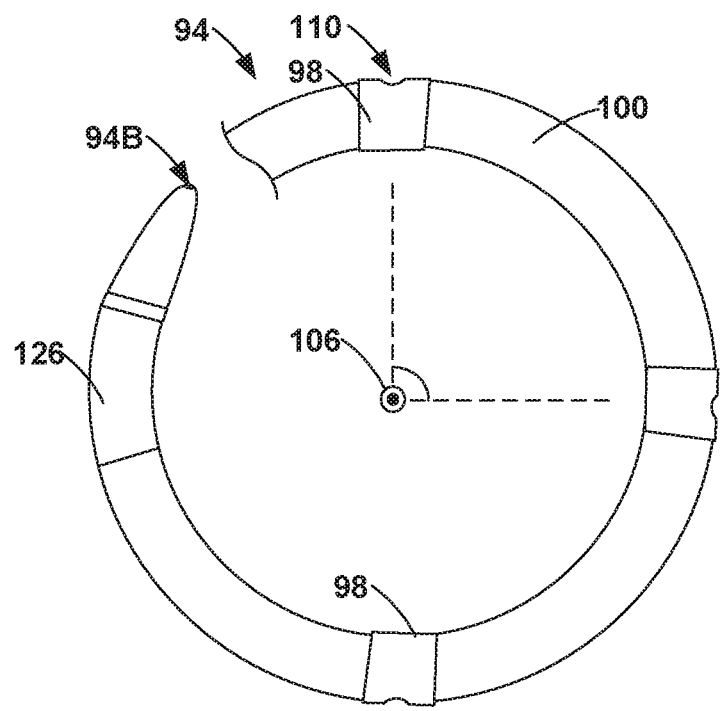
FIGS. 9A and 9B are example schematic views of the distal portion of the catheter of FIG. 7A viewed down the longitudinal axis showing the primary electrodes spaced at different rotational intervals along the tubular body.
Figure 9B:
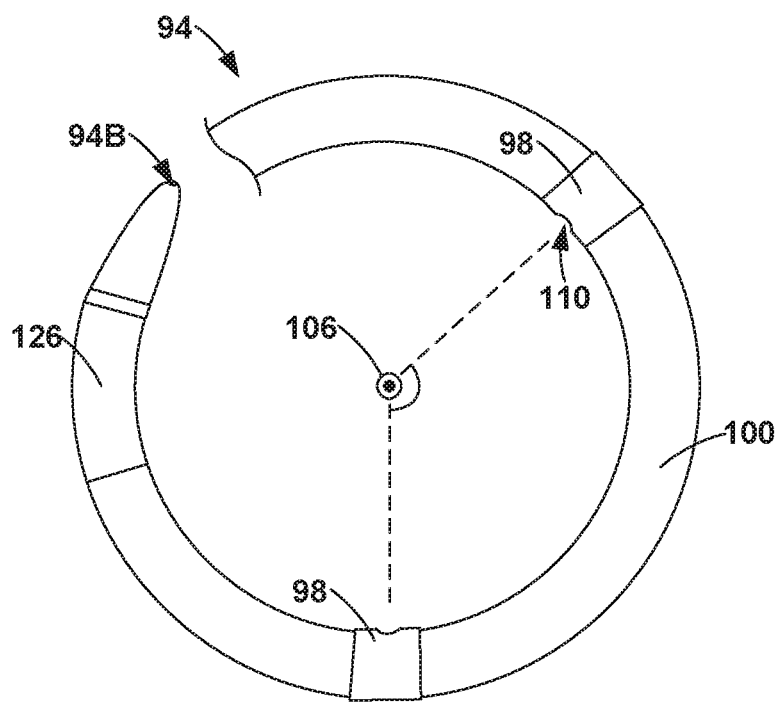

In some examples, primary electrodes 98 may be separated from one another to ensure a desired distribution or primary electrodes 98 along the curvilinear shape of distal portion 96. For example, when the curvilinear configuration is in the shape of a helix, primary electrodes 98 may be positioned at set rotational intervals along the helical-shape. FIGS. 9A and 9B are example schematic views of distal portion 96 viewed down central longitudinal axis 106 (e.g., longitudinal axis 106 extends into the page) showing primary electrodes 98 spaced at different rotational intervals along tubular body 100. In some examples, the spacing of primary electrodes 98 may be selected such that primary electrodes 98 are dispersed along the helical-shape at various degrees of rotation including, but not limited to, 90°, 120°, 180°, 270°, 360° (e.g., about one revolution), or other rotation intervals when distal portion 96 is in the fully deployed curvilinear configuration. Such spacings may allow for an even distribution of the pressure pulse waves produced by primary electrodes 98 along the entire wall of vessel 46. FIG. 9A, shows primary electrodes 98 spaced at approximately 90° intervals along the helical-shape of elongated member 94 and FIG. 9B shows primary electrodes 98 spaced at approximately 120° intervals along the helical-shape as two examples.

Electrode and body apertures 104 and 110 may be positioned on tubular body 100 to obtain a specific or random orientation when distal portion 96 is in the fully deployed curvilinear configuration. For example, electrode and body apertures 104 and 110 may be positioned so that apertures 104 and 110 face radially outward relative to the curvilinear shape and directed toward the inner wall of vessel 46 of the patient (e.g., FIG. 9A). In such configurations the resulting pressure pulse waves produced by electrodes 98 and 122 at electrode apertures 110 will be directed into the adjacent wall of vessel 46 to maximize the amount of energy directed into the target calcified lesion 44. In other examples, electrode and body apertures 104 and 110 may be positioned such that apertures 104 and 110 face radially inward relative to the curvilinear shape and are directed towards a central axis of vessel 46 (e.g., directed toward central longitudinal axis 106 as shown in FIG. 9B). The configuration may cause the resulting pressure pulse waves produced by electrodes 98 and 122 to be directed toward central longitudinal axis 106 rather than directly into the adjacent wall of vessel 46. The orientation may help distribute the resulting pressure pulse wave more evenly across the wall of vessel 46 by allowing the pressure pulse waves to propagate within fluid 40 held within vessel 46. The orientation may also help reduce the amount of localized heating that occurs at the wall of vessel 46 by directing the point where the electrical signal passes between one of primary electrodes 98 and secondary electrode 122 away from the interior surface of vessel 46.

Figure 10:
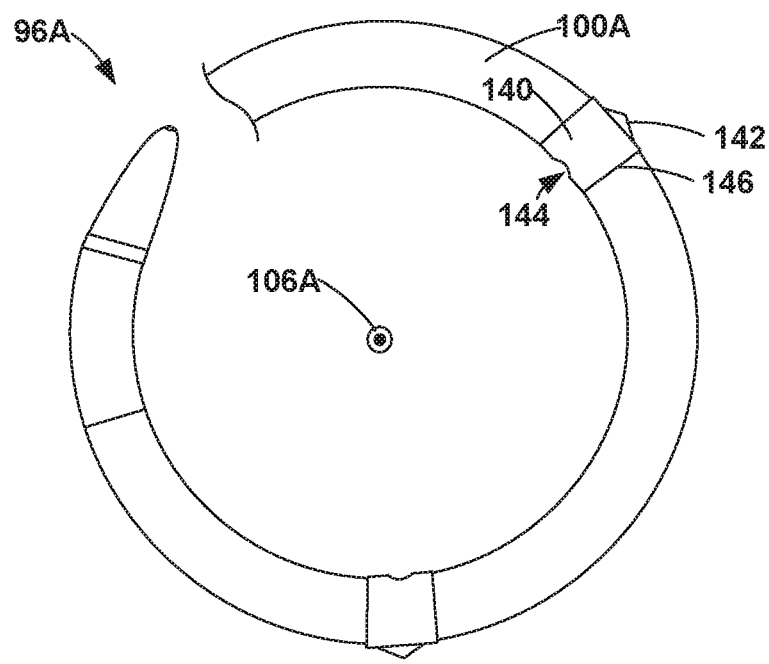
FIG. 10 is a schematic view of an example distal portion of an elongated member similar to the elongated member of FIG. 7A viewed down longitudinal axis showing primary electrodes that each include a protrusion spaced along a tubular body.

In some examples, primary electrodes 98 may include one or more protrusions that extend radially outward from the body of the respective electrode 98 to assist in the force delivery into the adjacent wall of vessel 46. FIG. 10 is a schematic view of an example distal portion 96A of an elongated member similar to elongated member 94, viewed down longitudinal axis 106A (e.g., longitudinal axis 106A extends into the page) showing primary electrodes 140 spaced along tubular body 100A, with each primary electrode 140 including a protrusion 142. Each of primary electrodes 140 may define a respective electrode aperture 144 and function substantially similar to primary electrodes 98 described above to cause cavitation of a fluid 40 in contact with primary electrodes 140.

Primary electrodes 140 may include a cylindrical body 146 coupled to tubular body 100A with at least one protrusion 142 extending radially outward and from cylindrical body 146 and positioned on a radially opposite side of cylindrical body 146 compared to electrode aperture 144. Primary electrodes 140 may be oriented so that when elongated member 94 is deployed in the curvilinear configuration (e.g., helical or spiral shape), protrusions 142 directly contact the interior surface of vessel 46 with electrode apertures 144 facing toward central longitudinal axis 106A. During the cavitation procedure, the pressure pulse waves produced by primary electrodes 140 will be directed toward longitudinal axis 106A causing a recoil effect that forces the respective primary electrode 140 radially outward toward the wall of vessel 46. Protrusions 142 will increase the localized force applied to the wall of vessel 46 and delivered to calcified lesion 44 located on or within vessel 46. The described configuration may help maximize the force from the pressure pulse wave delivered into the wall of vessel 46 while also minimizing the amount of heat or generated at the point of the electrical signal is transferred between the electrodes 140 and 122.

Figure 11A:
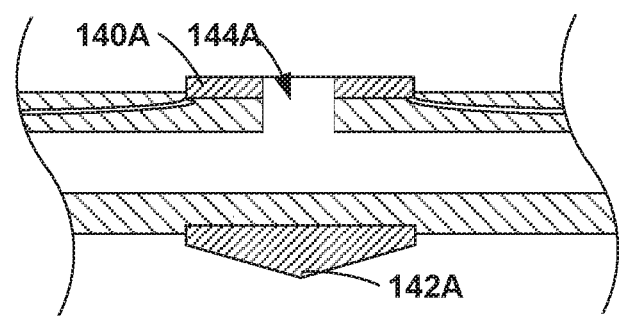
FIGS. 11A-11C are schematic cross-sectional views showing different example types of protrusions that may be incorporated with the primary electrodes of the catheter of FIG. 7A.
Figure 11B:
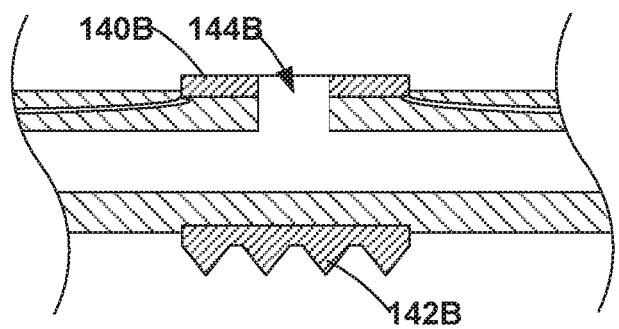
Figure 11C:
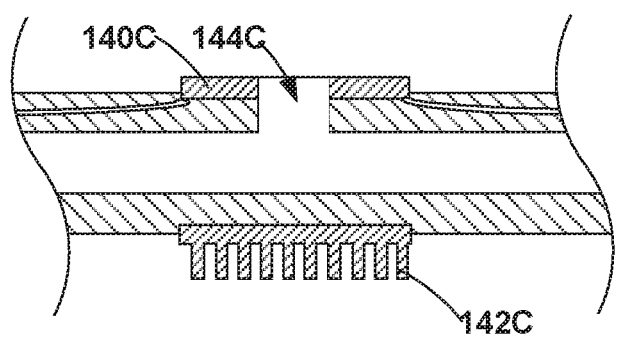

FIGS. 11A-11C are schematic cross-sectional views showing different example types of protrusions 142 that may be incorporated with primary electrodes 140. FIG. 11A illustrates a single protrusion 142A on primary electrode 140A in the form of a single triangular point projecting in a radially opposite direction of electrode aperture 144A. FIG. 11B and FIG. 11C each illustrate a plurality of protrusions 142B, 142C on primary electrodes 140B, 140C in the form of triangular points 142B or rod-like points 142C extending in a radially opposite direction of electrode apertures 144B and 144C. While the protrusions 142 are generally illustrated as either triangular or rod-like points, other geometric shapes are also envisioned and may be included on primary electrodes 140.

Figure 12:
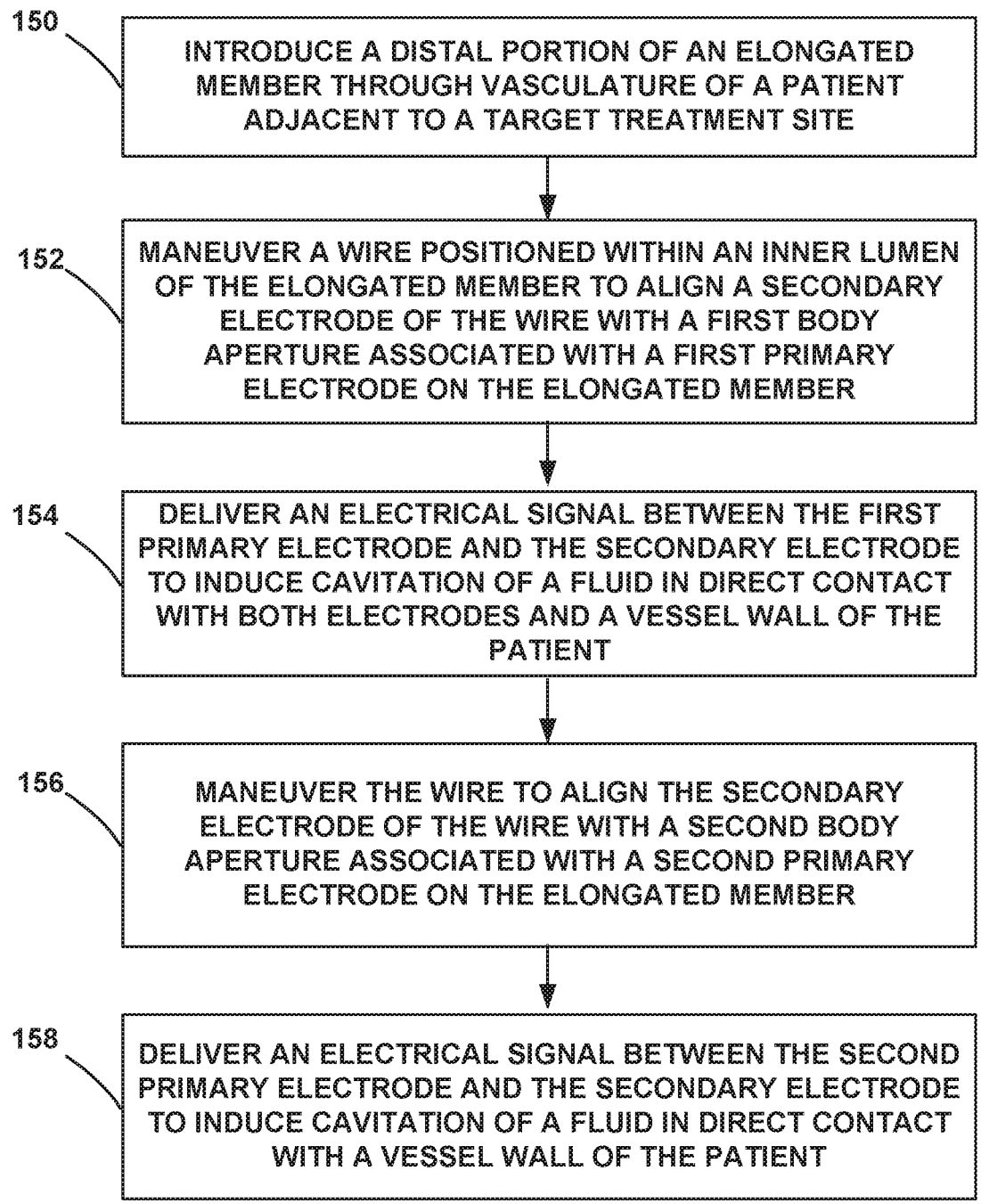
FIG. 12 is a flow diagram of an example technique of using the catheter assemblies described herein.

FIG. 12 and is a flow diagram of an example technique of using catheter assembly 10 or 90 described above. For simplicity of description, the techniques of FIG. 12 are described with reference to the various aspects of catheter assembly 90 of FIGS. 7A-11C, however, such descriptions are not intended to limit the techniques described to the particular devices of FIGS. 7A-11C. The techniques of FIG. 12 may be used with other catheters assemblies or catheters assemblies 10 and 90 of FIGS. 1A-11C may be used for other cavitation procedures.

The technique of FIG. 12 includes introducing a distal portion 96 of an elongated member 94 through vasculature of a patient adjacent to a target treatment site (150), maneuvering wire 120 positioned within inner lumen 102 of elongated member 94 to align secondary electrode 122 of wire 120 with a first body aperture 104 associated with a first primary electrode 98A of elongated member 94 (152), delivering an electrical signal between the first primary electrode 98A and secondary electrode 122 to induce cavitation of fluid 40 in direct contact with both electrodes 98A and 122 and a wall of vessel 46 (154), maneuvering wire 120 to align secondary electrode 122 of wire 120 with an second body aperture 104 associated with of a second primary electrode 98B of elongated member 14 (156), and delivering an electrical signal between the second primary electrode 98B and secondary electrode 122 to induce a second cavitation in fluid 40 in direct contact with both electrodes 98B, 122, and a wall of vessel 46 (158).

As described above, distal portion 96 may include one or more of primary electrodes 98 positioned along tubular body 100. Each of primary electrodes 98 may be coupled to energy source 20 using one or more electrical conductors 112 extending along tubular body 100 and within cable 114 while secondary electrode 122 maybe connected to energy source 20 using wire 120.

In some examples, each primary electrode 98 may include a respective electrode aperture 110 aligned with a corresponding body aperture 104 of tubular body 100 to provide fluid communication between the exposed surfaces of primary electrodes 98 and secondary electrode 122 contained within inner lumen 102. Additionally, or alternatively, primary electrodes 98 may be defined by a support structure 80 or shape member 108 with the primary electrodes created by portions of the structures have been exposed to form electrode and body apertures 104, 110. In some such examples, the support structure or shape member 108 may also act as the electrical conductor to couple primary electrodes 98 to energy source 20.

Distal portion 96 may be advanced to the target treatment site (150) using any suitable technique. For example, as described above, distal portion 96 may be navigated through tortuous vasculature of a patient using the aid of delivery sheath 130 or using wire 120 as a guide wire.

In some examples, such as where distal portion 96 is configured to transition to a curvilinear (e.g., helical) shape, delivery sheath 130 may be used physically restrain/bias distal portion 96 in a collapsed configuration (e.g., linearly-extended configuration) until distal portion 96 is adjacent the target treatment site. Once adjacent the target treatment site, delivery sheath 130 may be withdrawn proximally relative to elongate member 94 allowing distal portion 96 to transition into the deployed, curvilinear configuration within vessel 46 of a patient (e.g., shown in FIG. 8B). In other examples, distal portion 96 of elongated member 94 may be navigated through vasculature of a patient over wire 120. In some such examples, the proximal portion of wire 120 may be relatively stiff while the distal portion of wire 120 may be relatively flexible. The relatively stiff configuration of the proximal portion of wire 120 may help maintain distal portion 96 of elongated member 94 in the low profile or collapsed configuration by exerting a biasing force that overcomes force of tubular body 100 to transition to the deployed curvilinear configuration. As distal end 94B of elongated member 94 approaches the distal portion of wire 120, the increased flexibility of wire 120 may be insufficient to maintain distal portion 96 of elongated member 94 in the low profile or collapsed configuration, thereby allowing distal portion 96 to transition into the deployed curvilinear configuration.

The technique of FIG. 12 also includes maneuvering wire 120 within inner lumen 102 of elongated member 94 to align secondary electrode 122 with a first body aperture 104 associated with a first primary electrode 98A (152) (e.g., the distal most primary electrode 98 and body aperture 104 shown in FIG. 7C) and delivering an electrical signal between the respective primary and secondary electrodes 98A and 122 to induce cavitation of fluid 40 in direct contact with the electrodes (154). For instance, to deliver the electrical signal, the clinician may activate control mechanism 60 (e.g., via a foot petal) to begin delivery of the electrical signal.

As described above, the electrical signal may rapidly heat a portion of fluid 40 to produce short-lived gaseous steam/plasma bubbles within fluid 40. The steam/plasma bubbles may represent relatively low-pressure pockets of vapor generated from the surrounding fluid 40. The low-pressure steam/plasma bubbles eventually collapse in on themselves due to the relatively high pressure of the surrounding fluid 40. As steam/plasma bubbles collapse, the bubbles release a large amount of energy in the form of a high-energy pressure pulse wave 42 within fluid 40 that propagates through fluid 40 where they impact the wall of vessel 46 transmitting the mechanical energy of pressure pulse wave 42 into the tissue of a wall of vessel 46 and calcified lesion 44. The energy transmitted to calcified lesion 44 may cause the calcified lesion to fracture or beak apart.

As described above, the electrical signal may represent a corona, an electrical arc, a spark, or the like between primary electrode 98 and secondary electrode 122 in contact with fluid 40. The electrical signal may be a continuous wave signal or in the form of a plurality of pulses and may have any suitable electrical signal parameters for creating the cavitation. For example, the electrical signal may have an amplitude of about 500 volts (V) to about 5000 V, a pulse width of about 1 µs to about 200 µs, and a frequency of about 0.5 Hertz (Hz) to about 5 Hz.

The technique of FIG. 12 also includes repeating cavitation procedure by maneuvering wire 120 within inner lumen 102 of elongated member 94 to align secondary electrode 122 with a second body aperture 104 associated with a second primary electrode 98B (156) (e.g., the proximal most primary electrode 98 and body aperture 104 shown in FIG. 7C) and delivering an electrical signal between the primary and secondary electrodes 98B and 122 to induce cavitation of fluid 40 in direct contact with the electrodes (158). The cavitation procedure may be repeated for all or a select number of primary electrodes 98 to provide therapeutic treatment along one or more desired lengths of a wall of vessel 46.

Upon completion of the cavitation procedure, distal portion 96 may be removed from the vessel by, for example, advancing delivery sheath 130 back over distal portion 96. In some examples, a treatment balloon may be used after the cavitation procedure to dilate the vessel and increase the flow diameter of the vessel. The treatment balloon can be provided by a separate catheter that is introduced into to the target treatment site after the cavitation catheter (e.g., catheter 92) is removed from the patient. In some examples, the treatment balloon may include a therapeutic agent such as one or more of an anti-restenotic agent, an anti-proliferative agent, an anti-inflammatory agent, or other therapeutic agent over an exterior surface of the treatment balloon to help prevent restenosis of the vessel or otherwise treat the vessel or lesion. Example therapeutic agents may include, anti-proliferative agents such as paclitaxel, paclitaxel derivatives, or limus derivatives (e.g., sirolimus, everolimus, and the like), or anti-inflammatory agents such as non-steroid or steroid anti-inflammatory agents such as —COX inhibitors or glucocorticoids.

Various examples have been described. These and other examples are within the scope of the following claims.

What is claimed is:

1. A catheter assembly comprising:
  a catheter comprising a flexible elongated member comprising a distal portion, the distal portion comprising:
    a tubular body defining an inner lumen, the tubular body defining a plurality of body apertures that extend through a sidewall of the tubular body into the inner lumen; and
    a plurality of primary electrodes positioned along the tubular body; and
  a wire defining at least one secondary electrode, the wire being configured to be slidably moved through the inner lumen of the tubular body, wherein the wire and the plurality of primary electrodes are configured to electrically couple to an energy source that delivers an electrical pulse to a fluid in contact with the plurality of primary electrodes and the at least one secondary electrode to cause the fluid to undergo cavitation to generate a pressure pulse wave within the fluid.

2. The catheter assembly of claim 1, further comprising an energy source electrically coupled to the plurality of primary electrodes and the wire, wherein the catheter assembly and the energy source are configured such that, when the at least one secondary electrode is aligned with a respective body aperture of the plurality of body apertures while in the inner lumen of the tubular body, the energy source delivers an electrical pulse between a respective primary electrode of the plurality of primary electrodes adjacent to the respective body aperture and the at least one secondary electrode to cause the fluid in direct contact with the respective primary electrode and the at least one secondary electrode to undergo cavitation to generate the pressure pulse wave within the fluid.

3. The catheter assembly of claim 1, wherein a surface of each primary electrode of the plurality of primary electrodes is exposed to an external environment of the catheter.

4. The catheter assembly of claim 3, wherein the surface of each primary electrode of the plurality of primary electrodes forms an exterior surface of the catheter that defines a surface area of less than 0.1 mm$^2$.

5. The catheter assembly of claim 1, wherein the tubular body is configured to change from a collapsed configuration to a curvilinear configuration.

6. The catheter assembly of claim 5, wherein, when the tubular body is in the curvilinear configuration, at least a portion of the tubular body forms a helical-shape.

7. The catheter assembly of claim 1, further comprising an electrically insulating sheath over the wire, a portion of the wire being exposed to form the at least one secondary electrode.

8. The catheter assembly of claim 1, further comprising at least one electrical conductor within the tubular body, the at least one electrical conductor being configured to electrically connect the energy source to at least one electrode of the plurality of primary electrodes.

9. The catheter assembly of claim 8, where each primary electrode of the plurality of primary electrodes is electrically coupled to the at least one electrical conductor.

10. The catheter assembly of claim 1, wherein each primary electrode of the plurality of primary electrodes comprises an electrically conductive band coupled to the tubular body.

11. The catheter assembly of claim 1, wherein each primary electrode of the plurality of primary electrodes defines an electrode aperture that extends through the primary electrode and aligns with a corresponding body aperture of the plurality of body apertures.

12. The catheter assembly of claim 11, wherein for each primary electrode of the plurality of primary electrodes, the electrode aperture and the corresponding body aperture provide fluid communication between a surface of the primary electrode and the inner lumen.

13. The catheter assembly of claim 1, wherein the tubular body further comprises an electrically conductive support structure or shape member configured to electrically connect to the energy source, wherein the plurality of body apertures extend through the sidewall of the tubular body and the electrically conductive support structure or shape member, wherein, for each respective body aperture of the plurality of body apertures, a surface of the electrically conductive support structure or shape member is exposed by the respective body aperture and forms a respective primary electrode of the plurality of primary electrodes.

14. The catheter assembly of claim 1, wherein the elongated member is configured to position the plurality of primary electrodes in direct contact with a bodily fluid of a patient when deployed in vasculature of the patient.

15. The catheter assembly of claim 1, wherein the wire comprises a guidewire.

16. The catheter assembly of claim 1, wherein, to deliver the energy signal, the energy source is configured to deliver a plurality of electrical pulses each having a pulse width between 1 microsecond (μs) and 200 μs.

17. A catheter assembly comprising:
a catheter comprising a flexible elongated member comprising a distal portion, the distal portion comprising:
a tubular body comprising an inner liner, an electrically conductive support structure or shape member, and an outer jacket, wherein the tubular body defines an inner lumen, wherein the tubular body defines a plurality of body apertures that extend through a sidewall of the tubular body including the electrically conductive support structure or shape member into the inner lumen; and
a plurality of primary electrodes, wherein, within each respective body aperture of the plurality of body apertures, the electrically conductive support structure or shape member defines an exposed surface that forms a respective primary electrode of the plurality of primary electrodes; and
a wire comprising at least one secondary electrode, the wire being configured to be slidably moved through the inner lumen of the tubular body, wherein the wire and the electrically conductive support structure or shape member are configured to electrically couple to an energy source that delivers an electrical pulse to a fluid in contact with the plurality of primary electrodes and the at least one secondary electrode to cause the fluid to undergo cavitation to generate a pressure pulse wave within the fluid.

18. The catheter assembly of claim 17, further comprising:
an energy source electrically coupled to the electrically conductive support structure or shape member and the wire,
wherein the catheter assembly and the energy source are configured such that, when the at least one secondary electrode is aligned with a respective body aperture of the plurality of body apertures while in the inner lumen of the tubular body, the energy source delivers an electrical pulse between a respective primary electrode of the plurality of primary electrodes and the at least one secondary electrode to cause the fluid in direct contact with the respective primary electrode and the at least one secondary electrode to undergo cavitation to generate the pressure pulse wave within the fluid.

19. The catheter assembly of claim 17, wherein a surface of each primary electrode of the plurality of primary electrodes is exposed to an external environment of the catheter.

20. The catheter assembly of claim 17, wherein the tubular body is configured to change from a collapsed configuration to a curvilinear configuration.

21. The catheter assembly of claim 20, wherein, when the tubular body is in the curvilinear configuration, at least a portion of the tubular body forms a helical-shape.

22. The catheter assembly of claim 17, further comprising an electrically insulating sheath over the wire, a portion of the wire being exposed to form the at least one secondary electrode.

23. A method comprising:
introducing a catheter through vasculature of a patient to a target treatment site, the catheter comprising:
a flexible elongated member comprising a distal portion, the distal portion comprising:
a tubular body defining an inner lumen, the tubular body defining a plurality of body apertures that extend through a sidewall of the tubular body into the inner lumen; and
a plurality of primary electrodes positioned along the tubular body;
positioning the distal portion of the elongated member adjacent to the target treatment site;
slidably maneuvering a wire comprising at least one secondary electrode within the inner lumen of the elongated member to align the at least one secondary electrode of the wire with a respective body aperture of the plurality of body apertures, the respective body aperture being adjacent to a respective primary electrode of the plurality of primary electrodes; and
delivering, using an energy source, an electrical pulse between the respective primary electrode and the at least one secondary electrode, wherein delivery of the electrical pulse causes a fluid in direct contact with the respective primary electrode and the at least one secondary electrode to undergo cavitation that results in the generation of a pressure pulse wave within the fluid.

24. The method of claim 23, further comprising:
after delivering the electrical pulse, slidably maneuvering the wire within the inner lumen of the elongated member to align the at least one secondary electrode of the wire with a second respective body aperture of the plurality of body apertures, the second respective body aperture being adjacent to a second respective primary electrode of the plurality of primary electrodes; and
delivering a second electrical pulse using the energy source, wherein the electrical pulse is transmitted between the second respective primary electrode and the at least one secondary electrode through a fluid in direct contact with the second respective primary electrode and the at least one secondary electrode, the electrical pulse configured to cause the fluid to undergo cavitation to generate a pressure pulse wave within the fluid.

25. The method of claim 23, wherein delivering, using an energy source, an electrical pulse between the respective primary electrode and the at least one secondary electrode comprises delivering, using the energy source, an electrical pulse between each of the primary electrodes and the at least one secondary electrode at the same time to cause the fluid to undergo cavitation to generate a pressure pulse wave within the fluid.

26. The method of claim 23, wherein delivering, using the energy source, the electrical pulse between the respective primary electrode and the at least one secondary electrode comprises delivering the electrical pulse through a fluid in direct contact with the vasculature of the patient.

27. The method of claim 23, wherein a surface of each primary electrode of the plurality of primary electrodes is exposed to an external environment of the catheter.

* * * * *